United States Patent [19]

Hruska et al.

[11] Patent Number: 5,824,550
[45] Date of Patent: Oct. 20, 1998

[54] VOLTAGE-GATED CALCIUM CHANNEL AND ANTISENSE OLIGONUCLEOTIDES THERETO

[75] Inventors: Keith A. Hruska, St. Louis, Mo.; Peter A. Friedman, Lebanon; Elizabeth L. R. Barry, Hanover, both of N.H.; Randall L. Duncan, Indianapolis, Ind.

[73] Assignee: Barnes-Jewish Hopital, St. Louis, Mo.

[21] Appl. No.: 330,433

[22] Filed: Oct. 28, 1994

[51] Int. Cl.$^6$ .............................. C12N 5/10; C07H 21/00; C12Q 1/68

[52] U.S. Cl. .............................. 435/375; 435/6; 536/23.5; 536/24.3; 536/24.31; 536/24.33; 536/24.5

[58] Field of Search .............................. 536/23.5, 24.3, 536/24.31, 24.33, 24.5; 514/44; 435/6, 240.2, 375; 935/33, 34, 36, 8, 9, 11

[56] References Cited

U.S. PATENT DOCUMENTS

| | | | |
|---|---|---|---|
| 4,394,448 | 7/1983 | Szoka, Jr. et al. | 435/172 |
| 4,397,355 | 8/1983 | McLamore | 166/297 |
| 5,225,326 | 7/1993 | Bresser et al. | 435/6 |
| 5,585,479 | 12/1996 | Hoke et al. | 536/24.5 |

OTHER PUBLICATIONS

E. Uhlmann et al. Chemical Reviews 90 (4) (Jun. 1990) 543–84.

W. James Antivira Chem. & Chemotherapy 2(4) ('91) 191–214.

J. Holt et al. Mol. Cell. Biol. 8(2) (Feb. 1988) 963–73.

D. Tidd Anticancer Res. 10 ('90) 1169–82.

M. Cooney et al. Science 241 (Jul. 22, 1988) 456–9.

J. Milligan et al. J. Med. Chem. (Jul. 9, 1993) 36(14):1923–37.

C. Stein et al. Science 261 (Aug. 20, 1993) 1004–12.

B. Tseng et al. Cancer Gene Therapy 1(1) (Mar. 1994) 65–71.

W.-J. Ma et al J. Biol. Chem. 267(32) (Nov. 15, 1992) 22728–32.

J. Wetmur Crit. Rev. Biochem. & Mol. Biol. 26 (3/4) ('91) 227–59.

Yamaguchi, D.T. et al., *Journal of Biological Chemistry* 262: 7711–7718, "Parathyroid Hormone–activated Calcium Channels in an Osteoblast–like Clonal Osteosarcoma Cell" (Jun. 5, 1987).

Tanabe, T. et al. *Nature* 328, 313–318 "Primary Structure of the Receptor for Calcium Channel Blockers From Skeletal Muscle" (Jul. 23, 1987).

Yamaguchi, D.T. et al. *Journal of Biological Chemistry* 262: 14967–14973 "Protein Kinase C–activated Calcium Channel in the Osteo–blast–like Clonal Osteosarcoma Cell Line UMR–106*" (Nov. 5, 1987).

Ascenzi, A., *Journal of Biomechanical Engineering*, 110: 357–363 "The Micromechanics Versus the Macromechanics of Cortical Bone–A Comprehensive Presentation" (Nov. 1988).

Badley, J.E., et al., *Biotechniques* 6, 114–116 "A Simple Rapid Method for the Purification of Poly A+RNA" (1988).

Yamaguchi, D.T. et al., *Journal of Biological Chemistry* 264: 4383–4390 "Characterization of Volume–sensitive, Calcium–permeating Pathways in the Osteosarcoma Cell Line UMR–106–01*" (Mar. 15, 1989).

Mikami, A. et al. *Nature* 340, 230–233 "Primary Structure and Functional Expression of the Cardiac Dihydropyridine–sensitive Calcium Channel" (Jul. 20, 1989).

Rothenberg, M., et al., *Journal of National Cancer Inst.*, 81:1539–1544, "Oligodeoxynucleotides as Anti–Sense Inhibitors of Gene Expression: Therapeutic Implications" (Oct. 18, 1989).

Koch, W. J. et al., *Journal of Biological Chemistry* 265, 17786–17791 "cDNA Cloning of Dihydropyridine–sensitive Calcium Channel from Rat Aorta" Oct. 15, 1990.

Perez–Reyes, E., et al., *Journal of Biological Chemistry* 265, 20430–20436 "Molecular Diversity of L–type Calcium Channels" Nov. 25, 1990.

Iyer, R.P. et al., *J. Org. Chem.* 55:4693–4698 "The Automated Synthesis of Sulfur–Containing Oligodeoxyribonucleotides Using 3H–1,2–Benzodithiol–3–one 1,1–Dioxide as a Sulfur–Transfer Reagent" (1990).

Goodchild, J., *Bioconjugate Chemistry*, 1:1650167 "Conjugates of Oligonucleotides and Modified Oligonucleotides: A Review of Their Synthesis and Properties" (1990).

Hui, A. et al., *Neuron* 7, 35–44 "Molecular Cloning of Multiple Subtypes of a Novel Rat Brain Isoform of the $\alpha_1$ Subunit of Voltage–Dependent Calcium Channel" (Jul. 1991).

Snutch, T.P. et al.,*Neuron* 7, 45–57 "Distinct Calcium channels Are Generated by Alternative Splicing and Are Differentially Expressed in the Mammalian CNS" (Jul. 1991).

Naruse, K. et al.,*American Physiological Society* C1037–C1044, "Involvement of Stretch–Activated Ion Channels in $Ca^{2+}$ Mobilization to Mechanical Stretch in Endothelial Cells" (1993).

Barry, E. et al., *Biotechniques* 15: 1018–1020 "Introduction of Antisense Oligonucleotides into Cells by Permeabilization With Streptolysin O" (Dec. 1993).

*Primary Examiner*—Charles C. P. Rories
*Attorney, Agent, or Firm*—Senniger, Powers, Leavitt & Roedel

[57] ABSTRACT

An antisense oligonucleotide of 10 to 35 nucleotides in length that can hybridize with a region of the $\alpha_1$ subunit of the SA-Cat channel gene DNA or mRNA is provided, together with pharmaceutical compositions containing and methods utilizing such antisense oligonucleotide.

11 Claims, 6 Drawing Sheets

FIG. 2

```
ROB1              PWNVFDFLIVIGSIIDVILSEID..........................DPDESARISSAFFRLFRVMRLIKLLSRA
(SEQ ID NO: 7)    ||||||||||||||||||||||                          ||||||||||||||||||||||||||||
RabSkel1          PWNVFDFLIVIGSIIDVILSEIDTFLASSGGLYCLGGGCGNVDPDESARISSAFFRLFRVMRLIKLLSRA
(SEQ ID NO: 8)

ROB2              PWNVFDFLIVIGSIIDVILSETN...........................SAEENSRISITFFRLFRVMRLVKLLSRG
(SEQ ID NO: 9)    |||||||||||||||||||||||                           |||||||||||||||||||||||||||
RatBr2            PWNVFDFLIVIGSIIDVILSETNPAEHTQCSPSM.........SAEENSRISITFFRLFRVMRLVKLLSRG
(SEQ ID NO: 10)

ROB3              AWNTFDSLIVIGSIIDVALSEAD...........................NSEESNRISITFFRLFRVMRLVKLLSRG
(SEQ ID NO: 11)   ||||||||||||||||||||||                            ||||||||||||||||||||||||||||
RatBr3            AWNTFDSLIVIGSIIDVALSEADPSDSENIPLPTATPG....NSEESNRISITFFRLFRVMRLVKLLSRG
(SEQ ID NO: 12)
                                        └──── IVS3 ────┘                        └── IVS4 ──┘
```

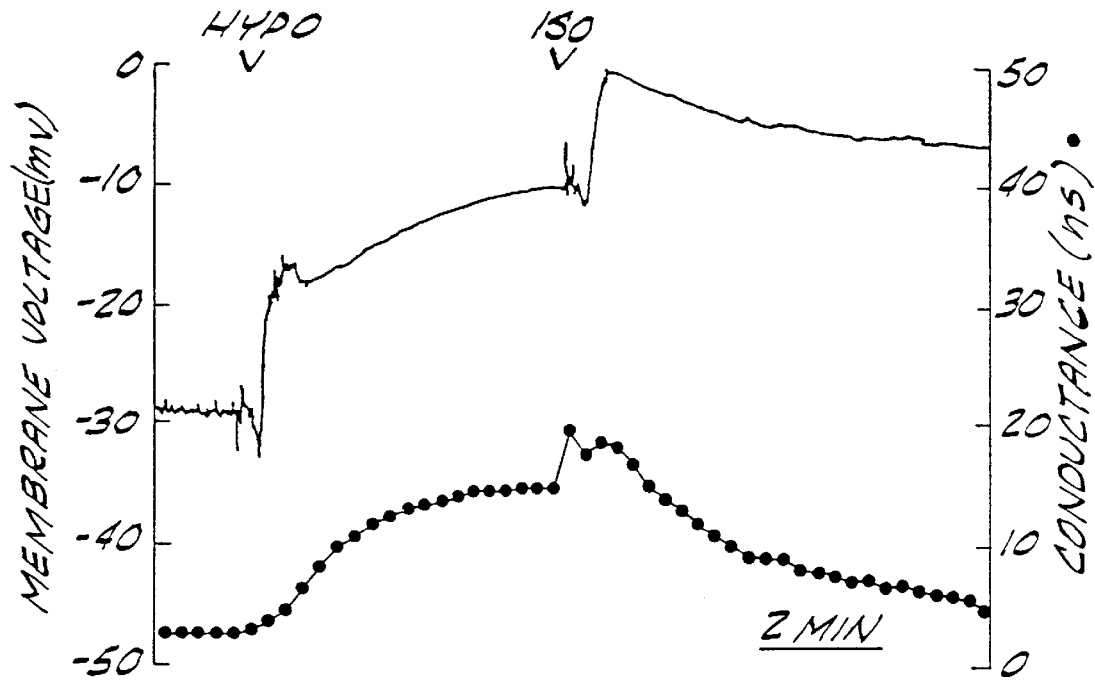

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 7860 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CCCAACACCT   TAATATTTAT   ATCTCCACGT   TGTTTTATTT   TTTTCCCCT    TGTTTTGGGG        60

GGCTTTTATT   TTCCTTTTGT   TTTTAAAATT   TTATCCTTGT   ATATCACAAT   AATGGAAAGA       120

AAGTTTATAG   TGTCTTTCAC   AAAGGAGCGT   AGTTTAAATG   CCCCGCCGCG   CCCGCGCCCG       180

CCCCTGCCAG   AACGGCGCTC   GGCGGCGCGG   CCCGGAGCGG   CGGCGGCGGT   GGCGGCGGCG       240
```

-continued

```
GCGGCCGTTC  CCGCGGGCTC  GCCCTCAGGT  GTTCGCGGCT  GCCGTCGCCG  AAGATCGCGG   300
GTCGGGGCCT  CGCGGCGATC  GCCCTGGGCG  GGCCGGAGAC  GCCTCGGGCC  CCCTGGCGGC   360
TCGGGGTCCA  CCCGGCGCCG  CGGGCCCGCC  GCTCTCCCTC  GCCTCGCCTT  TGCGCCTCTT   420
CTCGCTCTGC  CTCTCCATTT  ATTATTATTA  TCATTTTGT   TTTCAAATGG  TGTAGCCGCC   480
AGAGGTGCGG  TGCTAAATTC  TTGGAAGGGG  CCCGGATGTA  CTGAGGATGC  ATTACAATCT   540
CACGAAAGGA  GGCGGTAGTG  GAAAGCAGCA  GTTTTGGTG   TTTGGTGCAA  TAATGGGGAT   600
CAGGTAATCA  CCCGAAGGAG  CAAGAACCAC  TGCGGATCCA  CGGCTTCCTG  GATTTGCGCG   660
AGAGCCGCCG  GCCTCGGAGG  AGGGATCCAT  CCAGAGGCTC  GCGGGCTGTT  GCTGCATTTC   720
TTCCTCTTTG  TGGCTTCTCC  TTTCCAAGCA  GTTTTGGCC   AATGGTCAAT  GAAAACACGA   780
GGATGTACGT  TCCAGAGGAA  AACCACCAAG  GTTCCAACTA  TGGGAGCCCA  CGCCCAGCTC   840
ATGCCAACAT  GAATGCCAAT  GCAGCTGCAG  GACTTGCCCC  CGAGCACATC  CCTACTCCAG   900
GGGCAGCACT  GTCCTGGCAG  GCAGCCATCG  ATGCCGCCCG  GCAGGCCAAG  TTAATGGGCA   960
GTGCTGGCAA  TGCGACCATC  TCTACCGTCA  GTTCCACACA  GCGGAAGCGG  CAGCAGTATG  1020
GGAAACCCAA  GAAGCAGGGG  GGCACAACTG  CCACACGGCC  GCCCCGGGCT  CTGCTCTGCC  1080
TGACTCTGAA  GAACCCCATC  AGGAGGGCAT  GCATCAGCAT  TGTTGAATGG  AAACCATTTG  1140
AAATAATTAT  TTTATTGACG  ATTTTTGCCA  ATTGTGTGGC  CTTAGCAATC  TATATTCCCT  1200
TTCCGGAAGA  TGACTCCAAC  GCCACCAACT  CCAACCTGGA  ACGGGTGGAG  TATCTCTTCC  1260
TCATCATTTT  TACCGTGGAA  GCATTTTTAA  AAGTGATTGC  CTACGGACTA  CTCTTCCACC  1320
CCAACGCTTA  CCTCCGCAAC  GGTTGGAATT  TACTAGATTT  TATAATCGTG  GTTGTAGGGC  1380
TTTTTAGTGC  AATTTTAGAA  CAAGCAACCA  AAGCTGACGG  GGCCAACGCT  CTGGGAGGGA  1440
AAGGAGCGGG  ATTCGATGTG  AAGGCACTGA  GAGCTTTCCG  TGTGCTTCGT  CCCCTGCGGC  1500
TGGTGTCTGG  AGTCCCAAGT  CTCCAGGTGG  TCCTGAACTC  CATCATCAAG  GCCATGGTGC  1560
CCCTGCTGCA  CATTGCCCTC  CTCGTGCTCT  TCGTCATCAT  CATCTATGCC  ATTATCGGCC  1620
TGGAGCTCTT  CATGGGAAG   ATGCACAAGA  CCTGCTACAA  CCAGGAGGGC  ATAATAGATG  1680
TTCCAGCGGA  AGAGGATCCC  TCCCCTTGTG  CTTTGGAGAC  AGGCCATGGG  CGACAGTGTC  1740
AGAACGGGAC  CGTGTGCAAG  CCCGGGTGGG  ATGGGCCCAA  GCACGGCATC  ACCAACTTCG  1800
ACAACTTCGC  CTTCGCCATG  CTGACGGTGT  TCCAGTGTAT  CACCATGGAG  GGCTGGACAG  1860
ACGTGCTGTA  CTGGATGCAA  GACGCTATGG  GCTATGAGTT  GCCCTGGGTG  TATTTTGTCA  1920
GTCTGGTCAT  CTTTGGATCC  TTTTTCGTTC  TAAATCTGGT  TCTCGGTGTT  TTGAGCGGAG  1980
AGTTTTCCAA  AGAGAGGGAG  AAAGCCAAAG  CTCGAGGAGA  CTTCCAGAAG  CTTCGTGAGA  2040
AGCAGCAGCT  AGAAGAAGAT  CTCAAAGGCT  ACCTGGACTG  GATCACCCAG  GCGGAAGACA  2100
TAGACCCTGA  GAATGAGGAC  GAGGGCATGG  ATGAAGACAA  ACCCGAAAC   ATGAGCATGC  2160
CCACAAGTGA  GACTGAGTCT  GTCAACACCG  AAAACGTGGC  TGGAGGTGAC  ATCGAGGGTG  2220
AAAACTGTGG  AGCCCGGCTT  GCCCACCGGA  TCTCCAAATC  CAAGTTCAGC  CGCTACTGGC  2280
GCCGGTGGAA  TAGATTCTGC  AGAAGAAAGT  GCCGTGCCGC  AGTTAAGTCC  AACGTCTTCT  2340
ACTGGCTGGT  GATCTTCCTG  GTGTTCCTCA  ACACCCTCAC  CATTGCCTCC  GAACACTACA  2400
ACCAGCCTCA  TTGGCTCACA  GAAGTGCAAG  ACACGGCCAA  CAAGGCCCTC  CTGGCCCTTT  2460
TCACGGCAGA  AATGCTCCTG  AAGATGTACA  GCCTGGGTCT  GCAGGCCTAC  TTTGTATCCC  2520
TCTTCAACCG  CTTTGACTGT  TTCATTGTGT  GCGGGGGCAT  CCTGGAGACC  ATCCTGGTGG  2580
AGACGAAGAT  CATGTCGCCC  CTGGGCATCT  CCGTGCTGAG  ATGTGTGCGG  CTGCTCAGGA  2640
```

| | | | | | | |
|---|---|---|---|---|---|---|
| TTTTCAAGAT | CACCAGGTAC | TGGAACTCCC | TGAGCAACCT | CGTGGCGTCC | TTGCTGAACT | 2700 |
| CAGTGCGCTC | CATCGCCTCC | CTGCTGCTAC | TCCTCTTCCT | CTTCATCATC | ATCTTCTCCC | 2760 |
| TCCTGGGGAT | GCAGCTGTTT | GGTGGAAAGT | TCAACTTTGA | TGAGATGCAG | ACCCGTAGGA | 2820 |
| GCACGTTTGA | TAACTTCCCG | CAGTCTCTCC | TCACTGTGTT | TCAGATCCTG | ACCGGGGAGG | 2880 |
| ACTGGAATTC | GGTGATGTAT | GATGGGATCA | TGGCTTATGG | CGGCCCTCT | TTTCCAGGGA | 2940 |
| TGTTAGTCTG | TATTTACTTC | ATCATCCTCT | TCATCTGTGG | AAATTATATC | CTACTGAATG | 3000 |
| TGTTCTTGGC | CATTGCGGTG | GACAACCTGG | CTGATGCGGA | GAGCCTGACC | TCTGCCCAAA | 3060 |
| AAGAGGAAGA | AGAAGAGAAG | GAGAGAAAGA | AGCTGGCCAG | GACTGCCAGC | CCAGAAAAGA | 3120 |
| AACAGGAGGT | GATGGAGAAA | CCAGCAGTAG | AGGAGAGCAA | AGAGGAGAAA | ATTGAGCTGA | 3180 |
| AGTCCATTAC | AGCAGATGGA | GAATCCCGC | CCACTACCAA | GATCAACATG | GATGACCTCC | 3240 |
| AGCCCAGTGA | AAATGAGGAC | AAGAGTCCCC | ACTCCAACCC | AGACACTGCA | GGTGAAGAGG | 3300 |
| ATGAGGAGGA | GCCCGAGATG | CCTGTGGGCC | CACGCCCCG | GCCCCTGTCT | GAGCTGCACC | 3360 |
| TTAAGGAAAA | GGCAGTCCCC | ATGCCGGAAG | CCAGTGCATT | TTTCATCTTC | AGCCCAAACA | 3420 |
| ACAGGTTCCG | CCTGCAGTGC | CACCGCATTG | TCAATGACAC | GATCTTCACC | AACCTCATCC | 3480 |
| TCTTCTTCAT | TCTGCTCAGT | AGCATCTCCC | TGGCGGCTGA | GGACCCCGTC | CAGCACACCT | 3540 |
| CCTTCAGGAA | CCACATCCTA | GGCAATGCAG | ACTATGTCTT | CACTAGTATC | TTTACATTAG | 3600 |
| AAATTATCCT | TAAGATGACT | GCTTACGGGG | CTTTCCTGCA | CAAGGGCTCT | TTCTGCCGAA | 3660 |
| ATTACTTCAA | TATCCTGGAC | CTGCTGGTGG | TTAGCGTGTC | CCTCATCTCC | TTTGGCATTC | 3720 |
| AGTCCAGCGC | GATCAACGTT | GTGAAGATTT | TAAGAGTGCT | TCGTGTCCTC | AGGCCCCTGA | 3780 |
| GGGCCATCAA | CAGGGCCAAG | GGGCTAAAGC | ACGTCGTTCA | GTGTGTGTTT | GTGGCCATCC | 3840 |
| GGACCATTGG | AAACATTGTA | ATTGTCACCA | CTCTGCTGCA | GTTCATGTTC | GCCTGCATTG | 3900 |
| GGGTCCAGCT | CTTCAAGGGA | AAGCTCTATA | CCTGTTCGGA | TAGTTCCAAA | CAGACGGAGG | 3960 |
| CAGAATGCAA | GGGTAACTAT | ATAACATACA | AGACGGAGA | AGTTGACCAC | CCCATTATCC | 4020 |
| AGCCTCGAAG | TTGGGAGAAC | AGCAAGTTCG | ACTTTGACAA | TGTTCTGGCA | GCCATGATGG | 4080 |
| CCCTCTTTAC | CGTCTCCACC | TTCGAGGGGT | GGCCAGAGCT | GCTGTACCGC | TCCATTGACT | 4140 |
| CCCACACAGA | AGACAAGGGT | CCCATCTACA | ACTATCGTGT | GGAGATCTCC | ATCTTCTTCA | 4200 |
| TCATCTACAT | CATCATCATT | GCCTTCTTCA | TGATGAACAT | CTTCGTGGGT | TTCGTCATTG | 4260 |
| TCACCTTCCA | GGAGCAGGGG | GAACAAGAAT | ACAAGAACTG | TGAGCTGGAC | AAGAACCAGA | 4320 |
| GACAATGTGT | GGAATATGCC | CTCAAGGCCC | GACCCTTGCG | AAGGTACATC | CCCAAGAACC | 4380 |
| AGCACCAGTA | CAAAGTGTGG | TACGTGGTCA | ACTCCACCTA | CTTCGAGTAT | CTGATGTTCG | 4440 |
| TCCTCATCCT | GCTCAACACC | ATCTGCCTGG | CCATGCAGCA | CTACGGCCAG | AGCTGCCTCT | 4500 |
| TCAAAATCGC | CATGAATATA | CTCAACATGC | TTTTCACTGG | CCTCTTCACG | GTGGAGATGA | 4560 |
| TCCTGAAGCT | CATTGCCTTC | AAACCCAAGG | GTTACTTTAG | TGATCCCTGG | AATGTTTTTG | 4620 |
| ACTTCCTCAT | CGTCATTGGG | AGCATAATTG | ATGTCATTCT | CAGTGAAACT | AATCCAGCTG | 4680 |
| AACATACCCA | ATGCTCTCCC | TCTATGAGTG | CAGAGGAGAA | CTCCCGCATC | TCCATCACCT | 4740 |
| TCTTCCGCCT | CTTCCGGGTC | ATGCGCCTGG | TGAAGCTGCT | GAGCCGAGGG | GAAGGCATCC | 4800 |
| GGACCCTGCT | GTGGACCTTC | ATCAAGTCCT | TCCAGGCCCT | GCCCTATGTG | GCCCTTTTGA | 4860 |
| TTGTGATGCT | GTTCTTTATC | TATGCAGTGA | TTGGGATGCA | GGTATTTGGG | AAGATTGCCC | 4920 |
| TGAATGACAC | CACAGAGATC | AATCGGAACA | ACAACTTCCA | GACGTTCCCT | CAGGCTGTGC | 4980 |
| TACTGCTCTT | CAGGTGCGCC | ACTGGGGAGG | CCTGGCAGGA | TATCATGCTA | GCCTGTATGC | 5040 |

-continued

```
CAGGCAAGAA GTGTGCTCCA GAGTCTGAGC CCAGCAACAG CACGGAAGGG GAGACACCCT    5100
GTGGCAGCAG TTTCGCTGTC TTCTACTTCA TCAGCTTCTA CATGCTCTGT GCCTTCCTGA    5160
TCATCAACCT CTTTGTAGCT GTTATCATGG ACAACTTTGA CTACCTGACT AGGGATTGGT    5220
CTATCCTTGG TCCCCATCAC CTGGATGAAT TCAAGAGAAT CTGGGCCGAA TATGACCCTG    5280
AAGCCAAGGG TCGGATCAAA CACTTGGATG TGGTGACCCT CCTCCGTCGA ATTCAGCCCC    5340
CACTGGGTTT TGGGAAGTTG TGTCCTCACC GTGTGGCCTG CAAACGCCTG GTGTCCATGA    5400
ACATGCCTCT GAACAGTGAT GGGACGGTCA TGTTCAATGC TACACTGTTT GCCCTTGTCA    5460
GGACAGCCCT GAGGATCAAA ACAGAAGGGA ACCTAGAGCA AGCCAATGAG GAGCTGAGAG    5520
CCATCATCAA GAAAATCTGG AAGAGGACCA GCATGAAGCT GTTGGACCAG GTGGTGCCCC    5580
CTGCAGGTGA TGACGAGGTC ACAGTGGGCA AGTTCTATGC CACCTTCCTG ATCCAAGAGT    5640
ACTTCAGGAA ATTCAAGAAG CGAAAAGAGC AGGGGCTGGT CGGCAAGCCC TCGCAGAGGA    5700
ATGCACTGTC TCTGCAGGCT GGCTTACGCA CCTTGCATGA CATTGGGCCT GAGATCCGGA    5760
GAGCCATCTC TGGGGATCTG ACGGCTGAGG AGGAGCTGGA CAAGGCTATG AAGGAGGCAG    5820
TGTCTGCTGC CTCCGAAGAC GACATCTTCA GGAGGGCTGG AGGCCTGTTT GGCAACCACG    5880
TCAGCTACTA CCAGAGTGAC AGCAGGAGCA ACTTCCCTCA GACGTTTGCC ACCCAACGCC    5940
CACTGCACAT CAACAAGACA GGAACAACC AAGCGGACAC CGAATCACCG TCCCATGAGA    6000
AGCTGGTGGA CTCCACTTTC ACCCCCAGCA GCTACTCATC CACGGGCTCC AATGCCAACA    6060
TCAACAATGC CAACAACACT GCCCTGGGCC GCTTCCCCCA CCCTGCTGGC TACTCCAGCA    6120
CGGTCAGCAC TGTGGAGGGC CATGGGCCTC CCTTGTCCCC TGCTGTCCGG GTACAGGAGG    6180
CAGCATGGAA ACTCAGCTCT AAGAGGTGCC ACTCCCGAGA GAGCCAGGGG GCCACGGTGA    6240
GTCAGGATAT GTTTCCAGAT GAGACCCGCA GCAGCGTGAG GCTGAGCGAA GAAGTTGAGT    6300
ACTGCAGTGA GCCCAGCCTG CTCTCCACAG ATATACTCTC CTACCAGGAC GATGAAAACC    6360
GACAACTGAC CTGTCTAGAG GAGGACAAGA GGGAGATCCA GCCATCTCCG AAGAGGAGTT    6420
TCCTTCGCTC TGCCTCTCTA GGTCGAAGGG CCTCCTTCCA TCTGGAATGT CTAAAGCGAC    6480
AAAAGGATCA AGGAGGAGAC ATCTCTCAGA AGACAGCCTT GCCCTTGCAT CTGGTTCATC    6540
ACCAGGCATT GGCAGTGGCA GGCTTGAGCC CCCTCCTGCA GAGAAGCCAT TCTCCTTCCA    6600
CGTTTCCCAG GCCACGCCCC ACGCCCCCTG TCACTCCAGG CAGCCGGGGC AGGCCCCTAC    6660
AGCCCATCCC TACCCTGCGG CTGGAGGGGG CGGAGTCCAG TGAGAAACTC AACAGCAGCT    6720
TCCCGTCCAT CCACTGCAGC TCCTGGTCAG AGGAGACCAC AGCCTGTAGT GGGGGCAGCA    6780
GCATGGCCCG GAGAGCCCGG CCCGTCTCCC TCACCGTGCC CAGCCAGGCT GGAGCTCCAG    6840
GCAGACAGTT CCACGGCAGC GCCAGCAGCC TGGTGGAAGC GGTCTTGATT TCAGAAGGAC    6900
TGGGACAGTT TGCTCAAGAT CCCAAGTTCA TCGAGGTCAC CACACAGGAG CTGGCTGACG    6960
CCTGCGATAT GACAATAGAG GAGATGGAGA ACGCCGCAGA CAACATCCTC AGCGGGGGCG    7020
CCCAGCAGAG CCCCAACGGC ACCCTCTTAC CTTTTGTGAA CTGCAGGGAC CAGGGCAGG    7080
ACAGGGCTGT GGTCCCAGAG GACGAGAGCT GTGTATATGC CCTGGGGCGA GGCCAGAGCG    7140
AGGAAGCGCT CCCGGACAGC AGGTCCTATG TCAGCAACCT GTAGTCCGCA GGGCTGGCGA    7200
GACGCGGGTG TTTTTTATTC GTTTCAATGT TCCTAATGGG TTCGTTTCAG AAGTGCCTCA    7260
CTGTTCTCGT GACCTGGAGG TAACCGGAAC AGCGTCTTCA TTCACTGCTG TCGGGATAAG    7320
CCTCAGAGCT GGGCGGTGTA CGAAGTCGGC TTTTCAGGGG AGAAGGCCAA GGCCGTGGTG    7380
CGGGGGCTCC AGCACCTTCC CACGGCAGCA CCGCCCAAAG GACCCCACCC CCCCTAAGCA    7440
```

| | | | | | | |
|---|---|---|---|---|---|---|
| AAAGGGTGTT | TTCCCCTTGC | TTGTATAAAC | AGTCATTTGC | ACATGTTCTG | TCTGAGCCTG | 7500 |
| GCCGTCTCTA | TGGAGCAGGG | CCCCAGGGAT | CTATGGCAGG | AATGGCCAGT | GTCCCCAGTA | 7560 |
| GGAGCCGGAA | GGTGGCTGCA | AGGTTCCCAG | CAGTGCAGAT | CTGGTCCCTA | TTGCCCTTCA | 7620 |
| GGGACCCTTC | CCCTGCTGGA | ACTGAGGAGC | AGGTGCAGGA | GCCAGTGCAG | ACCACACCAC | 7680 |
| CTGCCCTCAG | CTAGCCAGAC | CTGGGGGCGC | AGGCTGCTTG | CCTGGTGCTC | TGGGTTTCAT | 7740 |
| AGTTTGATGG | TTCTTGTCAG | CATGTTGCGG | TTTTCTAGGT | TTTGATTTCT | TTATTACTAT | 7800 |
| TTGTTGTGTT | TTCCCACGGG | GAGGGAGGA | AGAAGAGCGT | TTACAACTGC | GCAGCTCACG | 7860 |

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | |
|---|---|---|---|
| CCTTCCGTGC | TGTTGCTGGG | CTCA | 24 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | |
|---|---|---|
| ACTCTGGAGC | ACACTTCTTG | 20 |

( 2 ) INFORMATION FOR SEQ ID NO:4:

( i ) SEQUENCE CHARACTERISTICS:
        ( A ) LENGTH: 844 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | | |
|---|---|---|---|---|---|---|
| GGGGGAGACT | GAGTATAAGA | ACTGTGAGCT | GGACAAGAAC | CAGCGCCAAT | GTGTGCAGTA | 60 |
| TGCCCTGAAG | GCCCGCCCGC | TGAGGTGTTA | CATCCCCAAA | AACCCATACC | AGTATCAGGT | 120 |
| GTGGTATGTC | GTCACTTCCT | CCTACTTTGA | ATACCTGATG | TTTGCTCTCA | TCATGCTCAA | 180 |
| CACTATCTGC | CTAGGCATGC | AGCATTACAA | CCAGTCGGAA | CAGATGAACC | ACATCTCGGA | 240 |
| CATCCTCAAT | GTGGCTTTCA | CCATCATCTT | CACCCTGGAG | ATGATCCTCA | AGCTCATAGC | 300 |
| TTTCAAGCCC | AGGGGCTATT | TTGGAGACCC | CTGGAACGTG | TTTGACTTTC | TAATCGTCAT | 360 |
| TGGCAGCATC | ATTGACGTTA | TCCTGAGTGA | GATCGATGAC | CCAGATGAGA | GCGCCCGCAT | 420 |
| CTCCAGTGCC | TTCTTCCGCC | TGTTCCGAGT | CATGCGACTG | ATCAAGCTGC | TGAGCCGGGC | 480 |
| GGAGGGTGTG | CGCACCCTGC | TCTGGACGTT | CACCAAGTCC | TTCCAGGCCC | TGCCGTATGT | 540 |
| GGCTTTGCTG | ATCGTCATGC | TCTTCTTCAT | CTACGCTGTC | ATCGGCATGC | AGATGTTCGG | 600 |
| GAAGATCGCC | ATGGTGGACG | GGACGCAAAT | AAACCGGAAC | AACAACTTCC | AGACTTTCCC | 660 |
| ACAAGCTGTG | CTGCTGCTCT | TCAGGTGTGC | CACAGGGGCA | GCCTGGCAGG | AGATCCTGCT | 720 |
| GGCCTGCAGC | TACGGGAAAC | GCTGCGACCC | GGAGTCTGAC | TACGCACCGG | GGAGGAGTA | 780 |
| CGCGTGTGGC | ACCAACTTTG | CCTACTACTA | CTTCATCAGC | TTCTACATGC | TCTGCGCCTT | 840 |

| | |
|---|---|
| CCTG | 844 |

(2) INFORMATION FOR SEQ ID NO:5:

(i) SEQUENCE CHARACTERISTICS:
        (A) LENGTH: 850 base pairs
        (B) TYPE: nucleic acid
        (C) STRANDEDNESS: single
        (D) TOPOLOGY: linear (xi) SEQUENCE DESCRIPTION: SEQ ID NO:5:

| | | | | | |
|---|---|---|---|---|---|
| GGGGGAACAA | GAATACAAGA | ACTGTGAGCT | GGACAAGAAC | CAGAGACAAT | GTGTGGAATA | 60 |
| TGCCCTCAAG | GCCCGACCCT | TGCGAAGGTA | CATCCCCAAG | AACCAGCACC | AGTACAAAGT | 120 |
| GTGGTACGTG | GTCAACTCCA | CCTACTTCGA | GTATCTGATG | TTCGTCCTCA | TCCTGCTCAA | 180 |
| CACCATCTGC | CTGGCCATGC | AGCACTACGG | CCAGAGCTGC | CTCTTCAAAA | TCGCCATGAA | 240 |
| TATACTCAAC | ATGCTTTTCA | CTGGCCTCTT | CACGGTGGAG | ATGATCCTGA | AGCTCATTGC | 300 |
| CTTCAAACCC | AAGGGTTACT | TTAGTGATCC | CTGGAATGTT | TTTGACTTCC | TCATCGTCAT | 360 |
| TGGGAGCATA | ATTGATGTCA | TTCTCAGTGA | AACTAATAGT | GCAGAGGAGA | ACTCCGCAT | 420 |
| CTCCATCACC | TTCTTCCGCC | TCTTCCGGGT | CATGCGCCTG | GTGAAGCTGC | TGAGCCGAGG | 480 |
| GGAAGGCATC | CGGACCCTGC | TGTGGACCTT | CATCAAGTCC | TTCCAGGCCC | TGCCCTATGT | 540 |
| GGCCCTTTTG | ATTGTGATGC | TGTTCTTTAT | CTATGCAGTG | ATTGGGATGC | AGGTATTTGG | 600 |
| GAAGATTGCC | CTGAATGACA | CCACAGAGAT | CAATCGGAAC | AACAACTTCC | AGACGTTCCC | 660 |
| TCAGGCTGTG | CTACTGCTCT | TCAGGTGCGC | CACTGGGGAG | GCCTGGCAGG | ATATCATGCT | 720 |
| AGCCTGTATG | CCAGGCAAGA | AGTGTGCTCC | AGAGTCTGAG | CCCAGCAACA | GCACGGAAGG | 780 |
| GGAGACACCC | TGTGGCAGCA | GTTTCGCTGT | CTTCTACTTC | ATCAGCTTCT | ACATGCTCTG | 840 |
| TGCCTTCCTG | | | | | | 850 |

(2) INFORMATION FOR SEQ ID NO:6:

(i) SEQUENCE CHARACTERISTICS:
        (A) LENGTH: 844 base pairs
        (B) TYPE: nucleic acid
        (C) STRANDEDNESS: single
        (D) TOPOLOGY: linear (xi) SEQUENCE DESCRIPTION: SEQ ID NO:6:

| | | | | | |
|---|---|---|---|---|---|
| GGGAGAAAAG | GAGTATAAGA | ACTGTGAGCT | GGACAAAAAT | CAGCGTCAGT | GTGTGGAATA | 60 |
| TGCCTTGAAG | GCCCGCCCCT | TAAGGAGATA | CATCCCCAAA | AACCCATACC | AGTACAAGTT | 120 |
| CTGGTACGTG | GTGAACTCCT | CGCCTTTCGA | ATATATGATG | TTTGTCCTCA | TCATGCTCAA | 180 |
| CACGCTCTGC | CTGGCCATGC | AGCACTATGA | GCAATCCAAG | ATGTTCAATG | ACGCCATGGA | 240 |
| CATTCTGAAC | ATGGTCTTCA | CGGGGGTCTT | CACCGTTGAG | ATGGTTTTGA | AAGTCATCGC | 300 |
| ATTTAAGCCC | AAGGGGTATT | TTAGTGACGC | CTGGAACACG | TTTGACTCCC | TCATCGTAAT | 360 |
| CGGCAGCATT | ATAGACGTGG | CACTCAGCGA | AGCTGACAAC | TCTGAAGAGA | GCAATAGAAT | 420 |
| CTCCATCACC | TTTTTCCGTC | TTTTCCGAGT | GATGCGGTTG | GTGAAGCTTC | TCAGCAGAGG | 480 |
| GGAAGGCATC | CGGACTCTGC | TATGGACCTT | CATTAAGTCC | TTCCAGGCAC | TCCCATATGT | 540 |
| CGCCCTCCTC | ATTGCCATGC | TCTTCTTCAT | CTACGCCGTC | ATTGGCATGC | AGATGTTTGG | 600 |
| GAAGGTTGCC | ATGAGAGATA | ACAACCAGAT | CAATAGGAAC | AACAACTTCC | AGACGTTTCC | 660 |
| CCAGGCAGTG | CTGCTGCTCT | TCAGGTGTGC | AACAGGGGAG | GCCCGGCAGG | AGATCATGCT | 720 |
| CGCCTGCCTC | CCTGGGAAGC | TGTGTGACCC | GGACTCAGAT | TACAACCCAG | GAGAGGAATA | 780 |

```
TACTTGTGGG  AGCAACTTTG  CCATTGTCTA  CTTCATCAGC  TTTTACATGC  TCTGCGCGTT           840

CCTG                                                                             844
```

( 2 ) INFORMATION FOR SEQ ID NO:7:

( i ) SEQUENCE CHARACTERISTICS:
        ( A ) LENGTH: 51 amino acid residues
        ( B ) TYPE: amino acid
        ( D ) TOPOLOGY: linear ( x i ) SEQUENCE DESCRIPTION: SEQ ID NO:7:

```
Pro  Trp  Asn  Val  Phe  Asp  Phe  Leu  Ile  Val  Ile  Gly  Ser  Ile  Ile  Asp
 1              5                       10                       15

Val  Ile  Leu  Ser  Glu  Ile  Asp  Asp  Pro  Asp  Glu  Ser  Ala  Arg  Ile  Ser
              20                       25                       30

Ser  Ala  Phe  Phe  Arg  Leu  Phe  Arg  Val  Met  Arg  Leu  Ile  Lys  Leu  Leu
              35                       40                       45

Ser  Arg  Ala
              50
```

( 2 ) INFORMATION FOR SEQ ID NO:8:

( i ) SEQUENCE CHARACTERISTICS:
        ( A ) LENGTH: 70 amino acid residues
        ( B ) TYPE: amino acid
        ( D ) TOPOLOGY: linear ( x i ) SEQUENCE DESCRIPTION: SEQ ID NO:8:

```
Pro  Trp  Asn  Val  Phe  Asp  Phe  Leu  Ile  Val  Ile  Gly  Ser  Ile  Ile  Asp
 1              5                       10                       15

Val  Ile  Leu  Ser  Glu  Ile  Asp  Thr  Phe  Leu  Ala  Ser  Ser  Gly  Gly  Leu
              20                       25                       30

Tyr  Cys  Leu  Gly  Gly  Gly  Cys  Gly  Asn  Val  Asp  Pro  Asp  Glu  Ser  Ala
              35                       40                       45

Arg  Ile  Ser  Ser  Ala  Phe  Phe  Arg  Leu  Phe  Arg  Val  Met  Arg  Leu  Ile
              50                       55                       60

Lys  Leu  Leu  Ser  Arg  Ala
 65                       70
```

( 2 ) INFORMATION FOR SEQ ID NO:9:

( i ) SEQUENCE CHARACTERISTICS:
        ( A ) LENGTH: 51 amino acid residues
        ( B ) TYPE: amino acid
        ( D ) TOPOLOGY: linear ( x i ) SEQUENCE DESCRIPTION: SEQ ID NO:9:

```
Pro  Trp  Asn  Val  Phe  Asp  Phe  Leu  Ile  Val  Ile  Gly  Ser  Ile  Ile  Asp
 1              5                       10                       15

Val  Ile  Leu  Ser  Glu  Thr  Asn  Ser  Ala  Glu  Glu  Asn  Ser  Arg  Ile  Ser
              20                       25                       30

Ile  Thr  Phe  Phe  Arg  Leu  Phe  Arg  Val  Met  Arg  Leu  Val  Lys  Leu  Leu
              35                       40                       45

Ser  Arg  Gly
              50
```

( 2 ) INFORMATION FOR SEQ ID NO:10:

( i ) SEQUENCE CHARACTERISTICS:
        ( A ) LENGTH: 62 amino acid residues
        ( B ) TYPE: amino acid
        ( D ) TOPOLOGY: linear ( x i ) SEQUENCE DESCRIPTION: SEQ ID NO:10:

| Pro | Trp | Asn | Val | Phe | Asp | Phe | Leu | Ile | Val | Ile | Gly | Ser | Ile | Ile | Asp |
| 1 | | | | 5 | | | | | 10 | | | | | 15 | |

| Val | Ile | Leu | Ser | Glu | Thr | Asn | Pro | Ala | Glu | His | Thr | Gln | Cys | Ser | Pro |
| | | | 20 | | | | | 25 | | | | | 30 | | |

| Ser | Met | Ser | Ala | Glu | Glu | Asn | Ser | Arg | Ile | Ser | Ile | Thr | Phe | Phe | Arg |
| | | 35 | | | | | 40 | | | | | 45 | | | |

| Leu | Phe | Arg | Val | Met | Arg | Leu | Val | Lys | Leu | Leu | Ser | Arg | Gly |
| | | 50 | | | | 55 | | | | | 60 | | |

( 2 ) INFORMATION FOR SEQ ID NO:11:

( i ) SEQUENCE CHARACTERISTICS:
        ( A ) LENGTH: 51 amino acids
        ( B ) TYPE: amino acid
        ( D ) TOPOLOGY: linear ( x i ) SEQUENCE DESCRIPTION: SEQ ID NO:11:

| Ala | Trp | Asn | Thr | Phe | Asp | Ser | Leu | Ile | Val | Ile | Gly | Ser | Ile | Ile | Asp |
| 1 | | | | 5 | | | | | 10 | | | | | 15 | |

| Val | Ala | Leu | Ser | Glu | Ala | Asp | Asn | Ser | Glu | Glu | Ser | Asn | Arg | Ile | Ser |
| | | | 20 | | | | | 25 | | | | | 30 | | |

| Ile | Thr | Phe | Phe | Arg | Leu | Phe | Arg | Val | Met | Arg | Leu | Val | Lys | Leu | Leu |
| | | 35 | | | | | 40 | | | | | 45 | | | |

| Ser | Arg | Gly |
| | | 50 |

( 2 ) INFORMATION FOR SEQ ID NO:12:

( i ) SEQUENCE CHARACTERISTICS:
        ( A ) LENGTH: 66 amino acid residues
        ( B ) TYPE: amino acid
        ( D ) TOPOLOGY: linear ( x i ) SEQUENCE DESCRIPTION: SEQ ID NO:12:

| Ala | Trp | Asn | Thr | Phe | Asp | Ser | Leu | Ile | Val | Ile | Gly | Ser | Ile | Ile | Asp |
| 1 | | | | 5 | | | | | 10 | | | | | 15 | |

| Val | Ala | Leu | Ser | Glu | Ala | Asp | Pro | Ser | Asp | Ser | Glu | Asn | Ile | Pro | Leu |
| | | | 20 | | | | | 25 | | | | | 30 | | |

| Pro | Thr | Ala | Thr | Pro | Gly | Asn | Ser | Glu | Glu | Ser | Asn | Arg | Ile | Ser | Ile |
| | | 35 | | | | | 40 | | | | | 45 | | | |

| Thr | Phe | Phe | Arg | Leu | Phe | Arg | Val | Met | Arg | Leu | Val | Lys | Leu | Leu | Ser |
| | 50 | | | | | 55 | | | | | 60 | | | | |

| Arg | Gly |
| 65 | |

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GCCGGATCCA TCGTCACCTT CCAGGAGCA    29

( 2 ) INFORMATION FOR SEQ ID NO:14:

( i ) SEQUENCE CHARACTERISTICS:
        ( A ) LENGTH: 29 base pairs (B) TYPE: nucleic acid
            (C) STRANDEDNESS: single
            (D) TOPOLOGY: linear (xi) SEQUENCE DESCRIPTION: SEQ ID NO:14:

ATGGAATTCG CCACRAAGAG GTTGATGAT 29

(2) INFORMATION FOR SEQ ID NO:15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:15:

GTGGGAATTC ATCAAGTCCT TCCAGGCCCT 30

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:16:

CAGGGGATCC AAGTTGTCCA TGATAACAGC 30

(2) INFORMATION FOR SEQ ID NO:17:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:17:

CCCGAATTCA KMGTGTTGAG CATGATGAG 29

VOLTAGE-GATED CALCIUM CHANNEL AND ANTISENSE OLIGONUCLEOTIDES THERETO

This invention was made with Government support under NASA grant NAG 2-791 awarded by the National Aeronautics and Space Administration and NIH grants AR 39561 and GM 34399 awarded by the National Institute of Health. The Government has certain rights in the invention.

BACKGROUND OF THE INVENTION

This invention relates to a voltage-gated calcium channel that stimulates bone formation in osteoblasts and mediates arterial tone in endothelial cells. More specifically, it relates to the gene for the voltage-gated calcium channel, antisense oligonucleotides useful for regulating the expression of the voltage-gated calcium channel gene and processes for the use of the antisense oligonucleotides to inhibit expression of the voltage-gated calcium channel, to inhibit bone formation, to mediate vascular blood pressure, and as an analytical tool useful for the development of strategies for responding to the bone loss caused by osteoporosis.

It has been known for a century that mechanical strain—whether resulting from physiological exercise or artificial means—increases bone formation and remodeling activity resulting in increased bone mass. Similarly, endothelial cells subjected to mechanical forces via fluid shear and vessel expansion have been shown to undergo increased cell proliferation and vasoactive secretions. Prior to the present invention, however, the precise molecular mechanism for enhancing the amount of bone deposited at the vector of force applied in osteoblasts and for increasing endothelial cell proliferation and vasoactive secretion, has remained unclear.

Voltage-gated calcium channels are members of a superfamily of cation channels, which also includes channels for $Na^+$, $K^+$ and divalent cations, i.e., $Ca^{2+}$. Calcium channels are responsible for the rapid entry of calcium into excitable cells upon membrane depolarization and are essential for excitation-contraction coupling in muscle, and the propagation of action potentials and neurotransmitter release in neurons. In addition, calcium channels regulate stimulus-secretion coupling during hormone release in endocrine glands. Much less is known about the roles of these calcium channels in other types of nonexcitable tissues.

Calcium channels may be sub-classified according to their electrophysiological behavior and pharmacological sensitivities. L-type calcium channels are defined pharmacologically by their sensitivity to three classes of calcium channel blockers, the phenylalkylamines, benzothiazepines and dihydropyridines. L-type calcium channels are multicomponent proteins made up of five subunits: $\alpha_1$, $\alpha_2$, $\delta$, $\gamma$, and $\beta$. The properties of calcium channels are largely conferred by the $\alpha_1$ subunit, which forms the actual pore site for the channel. The structure of the $\alpha_1$ subunit has been elucidated. It consists of four homologous repeats (I–IV) consisting of six membrane-spanning domains (S1–S6). The dihydropyridine receptor for the L-type channel is located on the carboxyl end of the $\alpha_1$ unit of the protein just beyond the S6 domain of the IV region.

Although common features of the structure of calcium channels have been established, variations in this structure have also been identified. At least six classes of calcium channel $\alpha_1$ subunit genes have now been identified, three of which are members of the dihydropyridine-sensitive L-type subfamily, including skeletal muscle (CaCh1), cardiac muscle (CaCh2) and neuroendocrine (CaCh3) isoforms. Still greater diversity is generated by alternative splicing.

Osteoblasts, the cells responsible for bone growth, have voltage-gated calcium (SA-Cat) channels that are known to play a role in bone formation. Recent studies indicate that a similar voltage-gated calcium channel is present in endothelial cells. Stretch-activated cation channels are, as the name suggests, activated by mechanical stimuli, e.g., mechanical loading or osmotic change. SA-Cat channels are voltage-independent, gadolinium-inhibitable and cation non-selective. In the present patent application we identify the osteoblast voltage-gated calcium channel as a member of the calcium channel superfamily, namely a CaCh2 isoform.

Osteoporosis is a debilitating disease characterized by the loss of normal bone density with the thinning of bone tissue and the growth of small holes in the bones. Osteoporosis frequently causes chronic pain, especially in the lower back, increased frequency of broken bones, loss of body height, and eventual loss of mobility and other body function. Osteoporosis has been classified into two categories. Primary osteoporosis, which includes post-menopausal osteoporosis, and secondary osteoporosis, which includes immobilization or disuse osteoporosis, together afflict approximately 20 million Americans.

Osteosclerosis is a lesser-known condition characterized by an abnormal increase in the density of bone mass. The condition occurs in various diseases and is often linked to poor circulation in the bone tissue, infection or tumor formation.

Hypertension is a common, generally asymptomatic disease marked by high blood pressure persistently exceeding 140/90. Essential hypertension, also known as primary hypertension, has no single known cause, and is the most prevalent form of hypertension, having been diagnosed according to some estimates, in over 50 million Americans. Secondary hypertension is linked to disease of the kidneys, lungs, glands or vessels. For example, pulmonary hypertension is a condition of unusually high pressure within the blood vessels of the lungs.

Antisense oligonucleotides are short synthetic nucleotide sequences formulated to be complementary to a portion of a specific gene or mRNA. They function by hybridizing to complementary sequences, resulting in selective arrest of expression of the complementary gene or mRNA. In particular, the cytoplasmic location of mRNA provides a readily accessible target for antisense oligonucleotides entering the cell. In addition to the use of antisense oligonucleotides as therapeutic agents due to their ability to block expression of a specific target protein, they also provide a useful tool for exploring regulation of the expression of a gene of interest in vitro and in tissue culture (see Rothenberg, M., et al., *Natl. Cancer Inst.*, 81:1539–1544, 1989).

The development of new therapeutic strategies against, and the creation of new analytical tools for, a better understanding of diseases such as osteoporosis, osteosclerosis, and hypertension, are greatly desired. It is particularly desirable to provide such tools and therapies that are highly specific to a target gene and protein, which at the same time, because of their specificity, do not substantially affect other proteins or body functions. The provision of antisense oligonucleotides for use in designing therapies and diagnostic tools for diseases and physiological responses related to voltage-gated calcium channel mediated physiological activities satisfies a long-sought need for such therapies and tools.

SUMMARY OF THE INVENTION

Among the objects of the invention, therefore, may be noted the provision of antisense oligonucleotides and pharmaceutical compositions that are capable of inhibiting the function of the voltage-gated calcium gene or mRNA and the provision of such oligonucleotides and compositions that serve as useful tools for exploring the regulation of gene expression in vitro and in tissue culture for the voltage-gated calcium. Also provided are a method for selectively blocking transcription or translation of the voltage-gated calcium channel gene and mRNA, for halting disease processes associated with the expression of that gene, and therapeutic procedures for the treatment of osteosclerosis and hypertension.

Briefly, therefore, the present invention is directed to an antisense oligonucleotide of 10 to 35 nucleotides in length that can hybridize with a region of the $\alpha_1$ subunit of the voltage-gated calcium channel gene DNA or mRNA.

In a further embodiment, the invention is directed to a pharmaceutical composition comprising at least one antisense oligonucleotide of 10 to 35 nucleotides in length that is capable of hybridizing with a region of the $\alpha_1$ subunit of the voltage-gated calcium channel gene DNA or mRNA and a pharmaceutically acceptable carrier.

In another aspect of the present invention, a method of inhibiting expression of the voltage-gated calcium channel gene is provided. The method comprises the steps of obtaining an antisense oligonucleotide of 10 to 35 nucleotides in length that can hybridize with a region of the $\alpha_1$ subunit of the voltage-gated calcium channel gene DNA or mRNA, combining the antisense oligonucleotide with a pharmaceutically acceptable carrier to create a pharmaceutically active mixture, and contacting the pharmaceutically active mixture with the $\alpha_1$ subunit of the voltage-gated calcium channel gene DNA or mRNA, thereby inhibiting expression of the voltage-gated calcium channel protein.

In yet another embodiment of the instant invention, a method of treating hypertension using the antisense oligonucleotides to the voltage-gated calcium channel gene is provided. The method includes the steps of obtaining a hypertensive-reductive amount of an antisense oligonucleotide 10 to 35 nucleotides in length that can hybridize with a region of the $\alpha_1$ subunit of the SA-Cat channel gene DNA or mRNA, combining the hypertensive-reductive amount of the antisense oligonucleotide with a pharmaceutically acceptable carrier to create a pharmaceutically active mixture, and contacting the pharmaceutically active mixture with the $\alpha_1$ subunit of the voltage-gated calcium channel gene DNA or mRNA of endothelial cells lining the blood vessels, inhibiting expression of the voltage-gated calcium channel protein and thereby causing a reduction in blood pressure.

In a further embodiment of the instant invention, a method of treating osteosclerosis using the antisense oligonucleotides to the voltage-gated calcium channel gene is provided. The method includes the steps of obtaining an osteosclerotic-reductive amount of an antisense oligonucleotide 10 to 35 nucleotides in length that can hybridize with a region of the $\alpha_1$ subunit of the voltage-gated calcium channel gene DNA or mRNA, combining the osteosclerotic-reductive amount of the antisense oligonucleotide with a pharmaceutically acceptable carrier to create a pharmaceutically active mixture, and contacting the pharmaceutically active mixture with the $\alpha_1$ subunit of the voltage-gated calcium channel gene DNA or mRNA of osteoblasts in a target tissue, inhibiting expression of the voltage-gated calcium channel protein and thereby causing a reduction in bone density in the target tissue.

Other objects and features will be in part apparent and in part pointed out hereinafter.

BRIEF DESCRIPTION OF THE DRAWINGS

SEQ ID NO.1 depicts the cDNA encoding for a region of the $\alpha_1$ subunit of the voltage-gated calcium channel protein.

FIG. 2 depicts a comparison of the deduced amino acid sequences of the UMR-106 clone with its corresponding CaCh isoform in the region where alternative splicing generates a deletion (ROB2 to the rat brain CaCh2 transcript (RatBr2).

FIG. 4(a) depicts the UMR-106 cell membrane potential and whole cell conductance response to hypotonic stretch and reversal to isotonic media. The cells had been exposed to chronic cyclic strain for nineteen hours. FIG. 4(b), depicts the same information as in FIG. 6(a), except that the cells had been loaded with the antisense oligonucleotide (SEQ ID NO:2).

FIG. 7(a) depicts the UMR-106 cells exposed to anti-streptolysin O but without exposure to the antisense oligonucleotide, exposed to 18 hrs of chronic cyclic strain prior to hypotonic stretch. FIG. 5(B) depicts the same procedure, but with exposure of the cells to the 20mer antisense oligonucleotide during the permeabilization.

FIG. 6 is a graphic representation of the effect of a sense 24mer oligonucleotide corresponding to the same sequence as in FIG. 4(b) on the response of UMR-106 cells to hypotonic stretch (as a control). Cells were loaded with the sense oligonucleotide in parallel with the antisense oligonucleotide used in FIG. 4(b) eighteen hours prior to study during which time the cells were exposed to chronic cyclic strain as described in Example 2 (Methods).

DETAILED DESCRIPTION OF THE PREFERRED EMBODIMENTS

Figure 1:
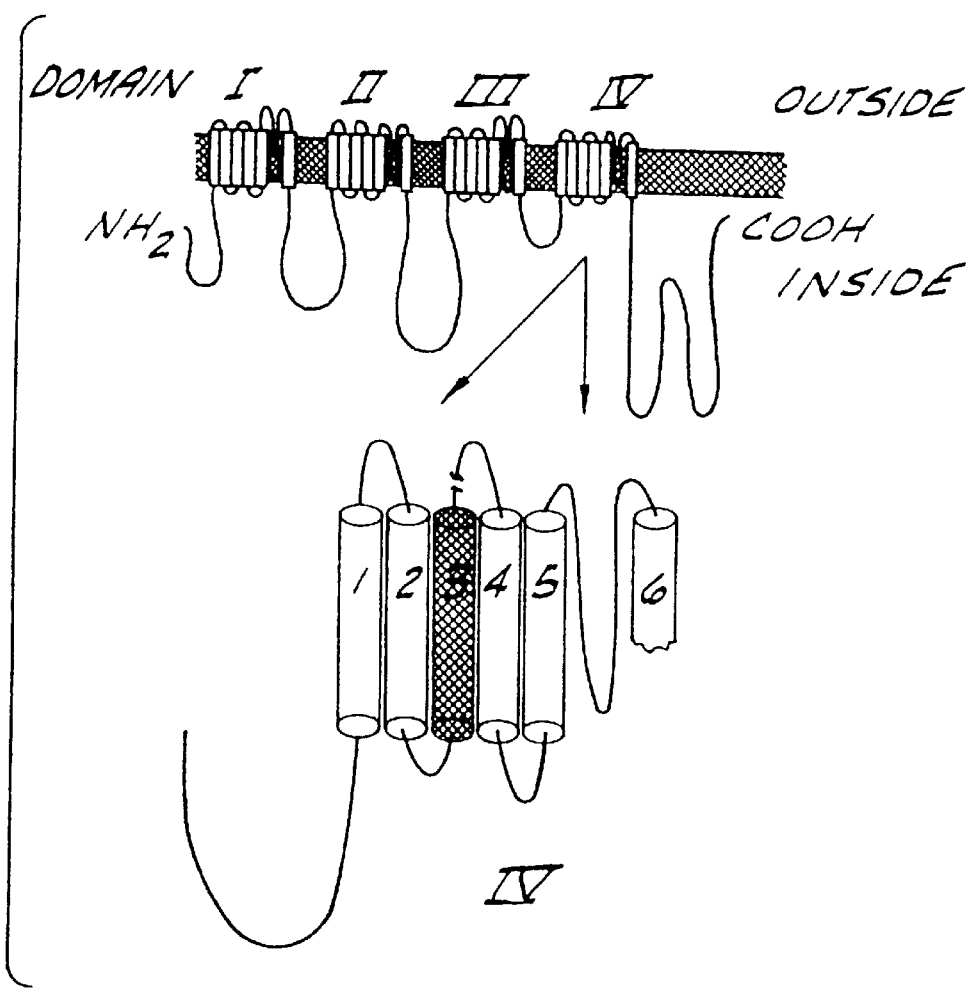
FIG. 1 is a schematic depiction of a model of an L-type calcium channel $\alpha_1$ subunit such as the voltage-gated calcium channel of the invention. The channel is composed of four homologous domains (I–IV) that are modeled to contain six transmembrane regions (S1–S6), and a segment (H5 or SS1–SS2) between the S5 and S6 domains, which is thought to loop into the membrane and line the external entrance to the pore of the channel. The IVS3 region is shaded to indicate that alternative splicing can generate two variants of this region. The hatched line just downstream of the S3 region indicates the site where a segment is omitted in the bone transcripts as a result of alternative splicing.

The term "oligonucleotide" as used herein means a molecule comprised of two or more deoxyribonucleotides, ribonucleotides, analogs or derivatives thereof.

"Oligonucleotide analog" or "oligonucleotide derivative," as those terms are used in conjunction with this invention, refer to moieties that function similarly to deoxyribonucleotides or ribonucleotides, but that have non-naturally occurring portions. Thus, oligonucleotide analogs may have altered sugar moieties or inter-sugar linkages. Exemplary among these are the phosphorothioate and other sulfur-containing species that are known to be useful in this art. They may also contain altered base units or other modifications consistent with the function of oligonucleotides in conjunction with this invention.

In accordance with the invention, it has been demonstrated that an isoform of the voltage-gated CaCh2b channel, an voltage-gated calcium channel protein, is activated by chronic mechanical loading and parathyroid hormone (PTH), two factors known to have anabolic or positive effects on bone formation in osteoblasts. Based on the ability of antisense oligonucleotides to the voltage-gated calcium channel protein to block the increase in whole cell conductance shown to be triggered by the application of chronic, intermittent mechanical strain to osteoblasts, it has further been demonstrated in accordance with this invention that the voltage-gated calcium channel is the signaling mechanism at the molecular level for increasing bone formation in response to mechanical strain.

As a consequence of these and other discoveries described herein, it is believed that application of an antisense strategy against expression of the voltage-gated calcium channel protein in osteoblasts will directly inhibit the abnormally-high bone density formation reflected in the condition known as osteosclerosis. Moreover, these discoveries provide an important analytical tool for and a critical link in the development of methods for the pharmacologic modulation of this channel for clinical treatment of osteoporosis. Thus, it is believed that stimulation of the voltage-gated calcium channel, which serves as a signal transducer for mechanical strain, for example by application of an agonist active in stimulating the expression of the voltage-gated calcium channel protein, will promote the beneficial properties of exercise on bone without the physical exertion that is difficult or impossible for elderly or paralyzed patients or for those unable to enjoy the beneficial effects of strain imposed by Earth's gravity due to extended space flight.

Recent laboratory research also has demonstrated that shear stress, or the mechanical stimulation of the endothelial cells lining the blood vessels by the flow of blood, plays a role in the control of blood pressure. Furthermore, stretching endothelial cells in vitro increases endothelin production and cell proliferation through an increase in intracellular calcium. The increase in intracellular calcium is blocked by gadolinium, a SA-Cat channel inhibitor, suggesting that the SA-Cat channel also transduces the mechanical strain induced by shear stress into cellular biochemical message either to relax or contract the blood vessel. Therefore, modulation of this channel by application of an antisense strategy is also believed to provide the clinician with a means of controlling blood pressure.

These discoveries and their application will be explained in greater detail below.

Mechanical strain increases bone formation and remodeling activity resulting in increased bone mass. Osteoblasts have stretch activated cation (SA-Cat) channels that are modulated by parathyroid hormone. Chronic, intermittent strain increases the sensitivity of SA-Cat channels to stretch increasing the number of channels open at any given time period and increasing single channel conductance. As a result, an increase in whole cell conductance is demonstrable. Furthermore, spontaneous activity of these channels is observed in chronically strained osteoblasts. These properties have not been previously demonstrated for SA-Cat channels, and they demonstrate that during mechanical loading of the osteoblast, SA-Cat channels are an integral component of the electrical environment and ion flux of the cell.

Chronic, intermittent strain applied to osteoblast-like cells not only affects ion conductance through SA-Cat channels, it also increases gene transcription for the bone matrix proteins. Application of cyclic strain for 24–72 hrs to osteoblast-like cell cultures increases type-1 procollagen message and type-1 collagen secretion. Chronic, intermittent strain also upregulates osteopontin message levels and osteocalcin secretion independent of, but additive to, 1,25 $(OH)_2$ Vitamin $D_3$ stimulation.

Calcium channel transcripts in UMR-106 cells were identified using the homology-based reverse transcriptase polymerase chain reaction. Primers were designed from regions that are highly conserved between L-type calcium channels to amplify essentially the entire fourth domain. An 850 base pair clone was isolated, which, upon sequencing, was found to be a CaCh2b variant. In addition, clones corresponding to CaCh1b and CaCh3b variants were isolated. The nucleotide sequence of the cDNA for the CaCh2b clone is set forth in Table 1. This Table depicts the nucleotide sequence of a partial cDNA clone encoding the fourth domain of the $\alpha_1$ subunit of L-type calcium channel isoforms CaCh1 (ROB1), CaCh2 (ROB2), and CaCh3 (ROB3) isolated from rat osteosarcoma UMR-106 cells. The putative transmembrane domains S1–S6 are indicated by heavy lines under the sequence. The symbol $\Delta$ indicates the site of omission of a segment by alternative splicing in the CaCh2b isoform.

Employing an antisense strategy, in accordance with the invention we have demonstrated the ability to inhibit the response of osteoblast-like cells to chronic, cyclic strain. Thus, we have shown that antisense oligonucleotides to the CaCh2 transcript eliminates the biophysical properties of the voltage-gated calcium channel in the cells. Voltage-gated calcium channel activity is eliminated by application of the antisense oligonucleotide.

Antisense therapy is the administration of exogenous oligonucleotides that bind to a target polynucleotide located within the cells. The term "antisense" refers to the fact that such oligonucleotides are complementary to their intracellular targets, e.g., the voltage-gated calcium channel gene or mRNA. See for example, Jack Cohen, *Oligodeoxynucleotides, Antisense Inhibitors of Gene Expression,* CRC Press, 1989; and *Synthesis* 1:1–5 (1988). The voltage-gated calcium channel antisense oligonucleotides of the present invention may be RNA or DNA that is complementary to and stably hybridizes with the DNA of, or the mRNA derived from, the voltage-gated calcium gene. Preferably, the antisense oligonucleotides are designed to maximize their specificity for the CaCh2 isoform relative to the CaCh1 and CaCh3 isoforms. Such specificity may be achieved by selecting sequences that

TABLE 1

| | | | | | | | | | |
|---|---|---|---|---|---|---|---|---|---|
| | 1 | | | | | | | | | 100 |
| RO81 (SEQ ID NO: 4) | GGGGGAGACT | GAGTATAAGA | ACTGTGAGCT | GGACAAGAAC | CAGGCGCCAAT | GTGTGCAGTA | TGCCCTGAAC | GCCCGCCCGG | TGAGGTGTTA | CATCCCCAAA |
| RO82 (SEQ ID NO: 5) | GGGGGAACAA | GAATACAAGA | ACTGTGAGCT | GGACAAGAAC | CAGAGACAAT | GTGTGGAATA | TGCCCTCAAG | GCCCGACCCT | TGCGAAGGTA | CATCCCCAAG |
| RO83 (SEQ ID NO: 6) | GGGAGAAAAG | GAGTATAAGA | ACTGTGAGCT | GGACAAAAAT | CAGGCGTCAGT | GTGTGGAATA | TGCCCTTGAAG | GCCCGCCCCT | TAAGGAGATA | CATCCCCAAA |
| | 101 | | | | | | | | | 200 |
| RO81 (SEQ ID NO: 4) | AACCCATACC | AGTATCAGGT | GTGGTATGTC | GTCACTTCCT | CCTACTTTGA | ATACCTGATG | TTTGCTCTCA | TCATGCTCAA | CACTATCTGC | CTAGGCATGC |
| RO82 (SEQ ID NO: 5) | AACCAGCACC | AGTACAAAGT | GTGGTACGTG | GTCAACTCCA | CCTACTTCGA | GTATCTGATG | TTCGTCCTCA | TCCTGCTCAA | CACCATCTGC | CTGGCCATGC |
| RO83 (SEQ ID NO: 6) | AACCCATACC | AGTACAAGTT | CTGGTACGTG | GTGAACTCCT | CGCCTTTCGA | ATATATGATG | TTTGTCCTCA | TCATGCTCAA | CACGCTCTGC | CTGGCCATGC |
| | | | | | | | | | IVS1 | |
| | 201 | | | | | | | | | 300 |
| RO81 (SEQ ID NO: 4) | AGCATTACAA | CCAGTCGGAA | CAGATGAACC | CATCCTCAAT | GTGGCTTTCA | CCATCATCTT | CACCCTGGAG | ATGATCCTCA | AGCTCATAGC | |
| RO82 (SEQ ID NO: 5) | AGCACTACGG | CCAGAGCTGC | CTCTTCAAAA | TATACTCAAC | ATGCTTTTCA | CTGGCCTCCTT | CACGGTGGAG | ATGATCCTGA | AGCTCATTGC | |
| RO83 (SEQ ID NO: 6) | AGCACTATGA | GCAATCCAAG | ATGTTCAATG | ACGCCATGGA | CATTCTGAAC | ATGGTCTTCA | CGGGGGTCTT | CACCGTTGAG | AAGTCATCGC | |
| | | | | | | | | IVS2 | | |
| | 301 | | | | | | | | | 400 |
| RO81 (SEQ ID NO: 4) | TTTCAAGCCC | AGGGGCTATT | TTGGAGACCC | CTGGAACGTG | TTTGACTTTC | TAATCGTCAT | TGGCAGCATC | TGAGCCGGGC | TCCTGAGTGA | GATCGATGAC |
| RO82 (SEQ ID NO: 5) | CTTCAAACCC | AAGGGTTACT | TTAGTGATCC | CTGGAATGTT | TTTGACTTCC | TCATCGTCAT | TGGGAGCATA | TGGGCCGTGC | TTCTCAGTGA | AACTAATAGT |
| RO83 (SEQ ID NO: 6) | AGCACTATGA | AAGGGCTATT | TTAGTGACAC | CTGGAACACG | TTTGACTTTC | TCATGTGTAAT | CGGCAGCATT | ATAGACGTGG | CACTCAGCGA | AGCTGACAAC |
| | | | | | | | | | | Δ |
| | 401 | | | | | | | | | 500 |
| RO81 (SEQ ID NO: 4) | CCAGATGAGA | GCGCCCGCAT | CTCCAGTGCC | TTCTTCCGCC | TGTTCCGAGT | CATGGCGACTG | ATCAACCTGC | TGAGCCGGGC | CCAGGGTGTG | CGCACCCTGC |
| RO82 (SEQ ID NO: 5) | GCAGAGGAGA | ACTCAAGTCC | TTCCAGGCCC | TTCTTCCGCC | TCTTCCGGGT | CATGCGCCAT | ATCACCC | GTGAAGCTGC | GGAAGGCATC | CGGACCCTG |
| RO83 (SEQ ID NO: 6) | TCTGAAGAGA | GCAATAGAAT | CTCCATCACC | TTTTTCCGTC | TTTTCCGAGT | GATGCGGTTG | ATCAAACCTGC | TCAGCAGAGG | GGAAGGCATC | CGGACTGTGG |
| | | | | | | | IVS-4 | | | |
| | 501 | | | | | | | | | 600 |
| RO81 (SEQ ID NO: 4) | TCTGGACGTT | CACCAAGTCC | TTCCAGGCCC | TGCCGTATGT | GGCTTTGCTG | ATCGTCATGC | TCTTCTTCAT | CTACGCTGTC | ATCGGCATGC | AGATCTTCGG |
| RO82 (SEQ ID NO: 5) | TGTTGGACCTT | CATCAAGTCC | TTCCAGGCCC | TGCCCTATGT | GGCCCTTTTG | ATTGTGATCC | TGTTCTTTAT | CTATGCAGTG | ATTGGGATGC | AGGTATTTGG |
| RO83 (SEQ ID NO: 6) | TATGGACCTT | CATTAAGTCC | TTCCAGGCAC | TCCCATATGT | GGCCATGTTC | ATTGTCATGC | TCTTCTTCAT | CTACGCCGTC | ATTGGCATGC | AGATGTTTGG |
| | | | | | | | IVS5 | | | |

TABLE 1-continued

| | | | | | | | | | | |
|---|---|---|---|---|---|---|---|---|---|---|
| | | | | | | | | | | 700 |
| (SEQ ID NO: 4) | 601 RO81 | GAAGATCGCC | ATGGTGGACG | GGACGCAAAT | AAACCGGAAC | AGACTTTCCC | ACAAGCTGTC | CTGCTGCTCT | TCAGGTGTGC | CACAGGGGCA |
| (SEQ ID NO: 5) | RO82 | GAAGATTGCC | CTGAATGACA | CCACAGAGAT | CAATCGGAAC | AGACGTTCCC | TCAGGCTGTG | CTACTGCTCT | TCAGGTGCGC | CACTGGGGAC |
| (SEQ ID NO: 6) | RO83 | GAAGGTTGCC | ATGAGAGATA | ACAACCAGAT | CAATAGGAAC | AGACGTTTCC | CCAGGCAGTG | CTGCTGCTCT | TCAGGTCTGC | AACAGGGGAG |
| | | | | | | | | | | 800 |
| (SEQ ID NO: 4) | 701 RO81 | GCCTGGCAGG | AGATCCTGCT | GGCCTGCAGC | TACGGGAAAC | GGAGTCTGA. | .....CTACG | CACCGGGGGA | GGAGTACGCG | TGTGGCACCA |
| (SEQ ID NO: 5) | RO82 | GCCTGGCAGG | ATATCATGCT | AGCCTGTATg | CCAGGCAAGA | AGAGTCTGAG | CCCAGCAACA | GCACGGAAGG | GGAGACACCC | TGTGGCACCA |
| (SEQ ID NO: 6) | RO83 | GCCCGGCAGG | AGATCATGCT | CACCTGCCTC | CCTGGGAAGC | GGACTCAGA. | .....TTACA | ACCCAGGACA | GGAATATACT | TGTGGGAGCA |
| | | | | | | | | | 850 | |
| (SEQ ID NO: 4) | 801 RO81 | ACTTTGCCTA | CTACTACTTC | ATCAGCTTCT | ACATGCTCTG | CGCCTTCCTG | | | | |
| (SEQ ID NO: 5) | RO82 | GTTTCGCTGT | CTTCTACTTC | ATCAGCTTCT | ACATGCTCTG | TGCCTTCCTG | | | | |
| (SEQ ID NO: 6) | RO83 | ACTTTGCCAT | TGTCTACTTC | ATCAGCTTTT | ACATGCTCTG | CGCGTTCCTG | | | | |
| | | | | | | IVS6 → | | | | | are not highly conserved between the isoforms. In general, only one or two (e.g., 1 in 20) base pair mismatches in a relatively short oligonucleotide are sufficient to exclude hybridization to non-targeted isoforms. The voltage-gated calcium channel antisense oligonucleotides of the present invention also include derivatives such as S-oligonucleotides (phosphorothioate derivatives or S-oligos) which exhibit voltage-gated calcium channel inhibitory action.

S-oligos (nucleoside phosphorothioates) are isoelectronic analogs of an oligonucleotide (O-oligos) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al., *J. Org. Chem.* 55:4693–4698 (1990), the disclosures of which are fully incorporated by reference herein. The above substitutions are known in the art to function to enhance the ability of the compositions to penetrate into the region of cells where the RNA whose activity is to be modulated is located. Others, such as alkyl phosphorothioate bonds, N-alkyl phosphoramidates, phosphorodithioates, alkyl phosphonates, and short chain alkyl or cycloalkyl structures may also be useful. Persons with ordinary skill in the art will be able to select other linkages for use in the practice of the invention.

Oligonucleotide analogs may also include species that include at least some modified base forms. Thus, purines and pyrimidines other than those normally found in nature may be so employed. Similarly, modifications on the furanose portions of the nucleotide subunits may also occur as long as the essential tenets of this invention are adhered to. All such analogs are comprehended by this invention so long as they function effectively to hybridize with DNA of or with mRNA derived from the voltage-gated calcium channel gene to inhibit the function of that DNA or mRNA.

The antisense oligonucleotides of this invention preferably comprise about 10 to about 35 bases, preferably from about 15 to 30, and most preferably about 18 to about 26. Two preferred embodiments of the antisense oligonucleotide sequences of the present invention are a 24 mer antisense oligonucleotide having SEQ. ID NO: 2 and a 20 mer antisense oligonucleotide having SEQ. ID NO: 3. These antisense oligonucleotides act just on the 5'-side of the S6 region of the IV domain of the voltage-gated calcium channel $\alpha_1$ subunit.

The oligonucleotides of this invention are designed to hybridize with DNA or mRNA of the voltage-gated calcium channel. Such hybridization, when accomplished, interferes with the normal function of these DNA/mRNA components. Such inhibited functions may include transcription of the DNA to mRNA, translocation of the RNA to the site of protein translation, and actual translation of protein from the mRNA. The overall effect of the interference caused by the antisense oligonucleotides of the invention is to cause inhibition of the expression of the voltage-gated calcium channel protein. Since it has been established that the voltage-gated calcium channel protein is a component of the signaling mechanism for stretch-induced increased bone formation in osteoblasts, such inhibition works directly to reduce the abnormally-high bone density exhibited in patients suffering from osteosclerosis. Similarly, it is believed that inhibition of voltage-gated calcium channel expression in endothelial tissue by antisense oligonucleotides will inhibit the enhanced cell proliferation and concomitant cellular changes which cause hypertension.

Although use of the antisense strategy is not directly applicable to therapies for treating osteoporosis, antisense oligonucleotides of the present invention represent important analytical tools for studying mechanisms to trigger, rather than inhibit, the expression of voltage-gated calcium channels in osteoblasts to signal enhanced bone matrix formation. Such further investigation using the antisense oligonucleotides as an analytical tool may provide the basis for developing agonists for the voltage-gated calcium channel signaling mechanism that can upregulate the level of bone matrix formation to counteract the loss of bone density caused by osteoporosis.

The present invention is additionally useful in diagnostics and in research in respects other than those specifically referenced above. It is believed that the voltage-gated calcium channels play roles in tissues not yet fully explored. Since the oligonucleotides of this invention hybridize to voltage-gated calcium channels, sandwich and other assays can easily be constructed to exploit this fact. Provision of means for detecting hybridization of oligonucleotides with voltage-gated calcium channels in tissue samples suspected of containing this channel may be accomplished by such means as enzyme conjugation, radiolabelling or other suitable detection systems.

Also included in the present invention are pharmaceutical compositions comprising an effective amount of at least one of the voltage-gated calcium channel antisense oligonucleotides of the invention in combination with a pharmaceutically acceptable carrier. The voltage-gated calcium channel antisense oligonucleotides are preferably coadministered with an agent which enhances the uptake of the antisense molecule by the cells. For example, the voltage-gated calcium channel antisense oligonucleotides may be combined with a lipophilic cationic compound, which may be in the form of liposomes. The use of liposomes to introduce nucleotides into cells is taught, for example, in U.S. Pat. Nos. 4,397,355 and 4,394,448, incorporated herein by reference. Alternatively, the voltage-gated calcium channel antisense oligonucleotides may be combined with a lipophilic carrier such as any one of a number of sterols including cholesterol, cholate and deoxycholic acid. A preferred sterol is cholesterol.

In addition, the voltage-gated calcium channel antisense oligonucleotide may be conjugated to a peptide that is ingested by cells. Examples of useful peptides include peptide hormones or antibodies. By choosing a peptide that is selectively taken up by the neoplastic cells, specific delivery of the antisense agent may be effected. The voltage-gated calcium channel antisense oligonucleotide may be covalently bound via the 5'H group by formation of an activated aminoalkyl derivative. The peptide of choice may then be covalently attached to the activated voltage-gated calcium channel antisense oligonucleotide via an amino and sulfydryl reactive hetero bifunctional reagent. The latter is bound to a cysteine residue present in the peptide. Upon exposure of cells to the SA-Cat channel antisense oligonucleotide bound to the peptide, the peptidyl antisense agent is endocytosed and the voltage-gated calcium channel antisense oligonucleotide binds to the target voltage-gated calcium channel mRNA to inhibit translation.

The voltage-gated calcium channel antisense oligonucleotides and the pharmaceutical compositions of the present invention may be administered by any means that achieve their intended purpose. For example, administration may be by parenteral, subcutaneous, intravenous, intramuscular, intraperitoneal, or transdermal routes. The dosage administered will be dependent upon the age, health, and weight of the recipient, type of concurrent treatment, if any, frequency of treatment, and the nature of the effect desired. For treatment of osteoscierosis, an osteosclerotic-reductive amount is to be administered. For treatment of hypertension, a hypertensive-reductive amount is to be applied.

Compositions within the scope of this invention include all compositions wherein the voltage-gated calcium channel antisense oligonucleotide is contained in an amount that is effective to achieve inhibition of expression of the voltage-gated calcium channel protein sufficient to, when applied to osteoblasts, ameliorate osteosclerosis, and when applied to endothelial tissue, cause a measurably significant reduction in blood pressure, either in localized tissue or system-wide. Although individual needs vary, determination of optimal ranges of effective amounts of each component is within the skill of the art.

In addition to administering the voltage-gated calcium channel antisense oligonucleotides as a raw chemical in solution, the voltage-gated calcium channel antisense oligonucleotides may be administered as part of a pharmaceutically active mixture or preparation containing suitable pharmaceutically acceptable carriers comprising excipients and auxiliaries that facilitate processing of the voltage-gated calcium channel antisense oligonucleotide into preparations that can be used pharmaceutically.

Suitable formulations for parenteral administration include aqueous solutions of the voltage-gated calcium channel antisense oligonucleotides in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, sodium carboxymethyl cellulose, sorbitol, and/or dextran. Optionally, the suspension may also contain stabilizers.

The antisense oligonucleotides of the present invention may be prepared according to any of the methods that are well known to those of ordinary skill in the art. Preferably, the antisense oligonucleotides are prepared by solid phase synthesis. See, Goodchild J. *Bioconjugate Chemistry*, 1:1650167 (1990), for a review of the chemical synthesis of oligonucleotides. Alternatively, the antisense oligonucleotides can be obtained from a number of companies which specialize in the custom synthesis of oligonucleotides.

The following examples illustrate the invention.

EXAMPLE 1

Materials—UMR-106 cells were obtained from American Type Culture Collection (Rockville, Md.). Cell culture media and serum were purchased from Sigma. Sources for other materials were as follows: Fast Track mRNA Isolation Kit (Invitrogen Corp., San Diego, Calif.), GeneAmp RNA PCR kit (Perkin Elmer Cetus, Norwalk, Conn.), pBluescript KS⁻ vector and XL-1 Blue bacteria (Stratagene, La Jolla, Calif.), Nuseive, Seakem and Seaplaque agarose (FMC Bioproducts, Rockland, Me.), Sequenase II kit (United States Biochemical Corp., Cleveland, Ohio), DNA ligase (Boehringer Mannheim, Indianapolis, Ind.), acrylamide (Gel-Mix 8, Gibco/BRL, Gaithersburg, Md.), DNA purification kit PZ523 Kit (5 Prime→3 Prime, Inc., Boulder, Colo.), Genescreen Plus nylon membrane (Du Pont NEN Research Products, Boston, Mass.). Labeled probes were prepared using the Riboprobe Gemini System (Promega Corp., Madison, Wis.). [$\alpha^{32}$P]UTP was purchased from Amersham. Oligonucleotides were synthesized commercially by Macromolecular Resources (Fort Collins, Colo.). Restriction enzymes were purchased from Gibco/BRL.

Cell Culture—UMR-106 cells were cultured in D-MEM/Ham's F-12 medium containing 5% fetal bovine serum. Cells were used between passages 3 and 17.

Purification of RNA—Poly (A⁺) RNA was isolated from cultured cells as described in Bradley, J. E., et al., *Biotechniques* 6, 114–116 (1988) using the FastTrack mRNA Isolation Kit. Briefly, UMR-106 cells were grown to confluence in P-100 culture dishes, washed in phosphate-buffered saline (137 mM NaCl, 2.6 mM KCl, 10 mM Na$_2$HPO$_4$, 1.8 mM KH$_2$PO$_4$, pH 7.4) and harvested by scraping. Cells were pelleted by centrifugation and homogenized with a polytron in the presence of 2% SDS. After incubation with proteinase K, the cell lysate was batch adsorbed to oligo (dT) cellulose and poly (A⁺) RNA was eluted in salt-free buffer. Approximately 20 μg of poly (A⁺) RNA was isolated from 1×10$_8$ cells.

cDNA synthesis and PCR—Poly (A⁺) RNA was reverse transcribed and cDNA was amplified using the GeneAmp RNA PCR kit as follows. Poly (A⁺) RNA, 250 ng, was incubated in a 20 μl reaction volume containing 2.5 U/μl Moloney murine leukemia viral reverse transcriptase, 2.5 μM random hexamers, 1.0 mM dNTPs and 1 U/μl RNase inhibitor in 50 mM KCl, 5 mM MgCl$_2$, and 10 mM Tris-HCl, pH 8.3, for 10 min at room temperature followed by 15 min at 42° C. and 5 min at 99° C. Subsequently, the samples containing first strand cDNA were brought up to a 100 μl reaction volume containing 10 mM Tris-HCl, pH 8.3, 50 mM KCl, 2.0 mM MgCl$_2$, 200 μM of each dNTP, 0.2 μM of each primer, and 2.5 units of AmpliTaq DNA polymerase and overlaid with 75 μl of mineral oil. PCR was performed on an automated thermal cycler (Model 480, Perkin-Elmer Cetus) that was programmed to repeat the following cycle 30 times: 60 s at 94° C., 60 s at 60° C. and then 120+2 s/cycle at 72° C.

PCR primers—Oligodeoxynucleotide PCR primers were designed from regions that are highly conserved between L-type calcium channels using the following published sequences: CaCh 1 (rabbit skeletal muscle isoform) Tanabe, T. et al. (1987) *Nature* 328, 313–318, CaCh2 (rat cardiac muscle isoform) Snutch, T. P. et al. (1991) *Neuron* 7, 45–57 and CaCh3 (rat neuroendocrine isoform) Hui, A. et. al. (1991) *Neuron* 7, 35–44. Two pairs of primers were used. One set spanned the entire calcium channel domain IV: upstream primer-1 (UP-1): 5'-gcc ggatccatcgtcaccttccaggagca-3'(SEQ ID NO: 13); and downstream primer (DP-1): 5'-atggaattcgccacraagaggttgatgat-3' (r=a or g)(SEQ ID NO: 14). A second set spanned domain IVS5 through IVS6: upstream primer-2 (UP-2 ): 5'-gtg ggaattcatcaagtccttccaggccct-3'(SEQ ID NO: 15) and downstream primer-2 (DS-2): 5'-cagg ggatccaagttgtccatgataacagc-3'(SEQ ID NO: 16). An additional downstream primer, (DS-3): 5'-ccc gaattcakmgtgttgagcatgatgag-3' (k=t or g, m=a or c)(SEQ ID NO: 17), was designed from sequence in the IVS1 segment of the UMR-106 ROB1 and ROB3 clones to be used with the UP-1 primer to amplify only the 5' end of those clones. Bam H1 or Eco R1 restriction sites (underlined) were included near the 5' ends of the primers to facilitate directional subcloning.

Cloning PCR products—The products of the PCR reaction were directionally cloned into the pBluescript KS⁻ vector. Initially, one half of each PCR reaction was analyzed by electrophoresis on 1% Nuseive/1% Seakem agarose gels. For subcloning, the remaining reaction product was purified by phenol/chloroform/Isoamyl alcohol (25:24:1) extraction and ethanol precipitation, digested with Eco R1 and Bam H1, and isolated as a band from a low melting temperature 1% Seaplaque agarose gel. The vector was also digested with Eco R1 and Bam H1 and isolated on a low melt agarose gel. The ligation reaction was carried out in a 50 µl volume containing 5 U T4 DNA ligase in 66 mM Tris-HCl, 5 mM $MgCl_2$, 1 mM dithioerytritol, 1 mM ATP, pH 7.5. Agarose gel slices containing the PCR product or vector were melted at 70° C. for 10 min before the addition of 2–4 µl to the reaction. The ligation reaction was incubated at 15° C. for 16 h. One tenth of each ligation reaction was used to transform XL-1 Blue bacteria. Competent bacteria were prepared by the calcium chloride method and transformed according to a standard protocol (Sambrook, J., et al., *Molecular Cloning: A Laboratory Manual*, 2nd Ed., 1989). Transformants were plated onto LB (10 g/L tryptone, 5 g/L yeast extract, 10 g/L NaCl) agar plates containing 50 µg/ml ampicillin and 12.5 µg/ml tetracycline that had been coated with 10 µl of 2% 5-bromo-4-chloro-3-indoyl-β-D-galactopyranoside and 40 µl of 100 mM isopropyl-β-D-thiogalactopyranoside. Individual white colonies were picked and grown overnight in 5 ml of LB medium containing 50 µg/ml ampicillin at 37° C. Plasmid DNA was prepared from 3.0 ml of overnight culture by alkaline lysis. The presence of an appropriately sized insert was confirmed by Eco R1 and Bam H1 restriction digestion of the plasmid DNA.

Sequencing of Double-Stranded DNA Templates— Plasmid DNA, 5 µg, was denatured in 200 mM NaOH, 0.2 mM EDTA for 30 min at 37° C., neutralized and precipitated in ethanol. Sequencing was by the dideoxynucleotide chain termination method using the Sequenase II kit. The products were separated by electrophoresis on 8.0% acrylamide gels. Some sequencing was also performed on an automated instrument (Applied Biosystems, Foster City, Calif.) using plasmid DNA purified with the PZ523 Kit. The final sequences were determined from both strands of the cDNA. Sequence analysis was performed using on-line software from the Genetics Computer Group, Inc. (Madison, Wis.).

Northern Blot Analysis—Poly (A+) RNA was electrophoresed on a 0.75% agarose/formaldehyde denaturing gel and eletrophoretically transferred to Genescreen Plus nylon membrane. The membranes were UV-crosslinked and baked for 2 h at 80° C. under vacuum. Prehybridization was carried out in 0.25 m $NaPO_4$, pH 7.2, 0.25 M NaCl, 1 mM EDTA, 50% formamide, 6% SDS at 55° C. for 1 hr. [$^{32}$P]-labeled RNA probes were synthesized form linearized cDNA templates using the Riboprobe Gemini System. Hybridization with riboprobes, $2 \times 10^6$ cpm/ml, was under the same conditions as the prehybridization for 20 h. The membranes were washed twice in 0.3M NaCl, 0.03M $Na_3$Citrate, pH 7.0 (2× SSC) for 5 min at room temperature; twice in 0.25M $NaPO_4$, pH 7.2, 2% SDS, 1 mM EDTA for 30 min at 65° C.; and twice in 0.04 M $NaPO_4$, pH 7.2, 1% SDS, 1 mM EDTA for 30 min at 65° C. To decrease the background, the membranes were subsequently rinsed three times in 2× SSC for 5 min at room temperature, incubated in 2× SSC containing 1 µg/ml RNase A for 15 min at room temperature, and washed twice in 0.04M $NaPO_4$, pH 7.2, 1% SDS, 1 mM EDTA for 30 min at 65° C. Autoradiography was carried out at −70° C. with an intensifying screen. Hybridization with a riboprobe for human β-actin was used as a positive control.

RESULTS

Homology-based reverse transcriptase-PCR was used to identify transcripts for L-type calcium channels that are present in UMR-106 cells. Primers were designed from regions that are highly conserved between L-type calcium channels to amplify essentially the entire fourth domain (FIG. 1). Three types of cDNA clones were isolated, corresponding to all three of the known L-type calcium channel genes. The CaCh2 isoform (Table 1, ROB2), 850 base pairs, is identical to the rat brain rbC-I transcript (22), except for a 33 base pair (11 amino acids) deletion (FIG. 2) in the S3–S4 linker. This isoform has subsequently been determined (see below) to be a close isoform of the voltage-gated calcium channel gene.

Alternative splicing in the fourth domain of L-type calcium channels can potentially give rise to four variants of CaCh2 (CaCh2a, b, c, d) transcripts (Perez-Reyes, E., et al., *J. Biol. Chem.* 265, 20430–20436 (1990)). This occurs through the use of an alternate splice acceptor site or an exon skipping event in the extracellular IVS3-S4 linker that produces two sizes of transcripts. In addition, mutually exclusive splicing of alternate exons (approximately 50% homologous) encoding the transmembrane IVS3 domain occurs in CaCh2 transcripts (Perez-Reyes, Supra).

According to the Perez-Reyes nomenclature, each of the three L-type CaCh transcripts isolated from UMR-106 cells are of the b type since they contain a specific IVS3 variant and they lack a portion of the IVS3-S4 linker region.

Figure 3:
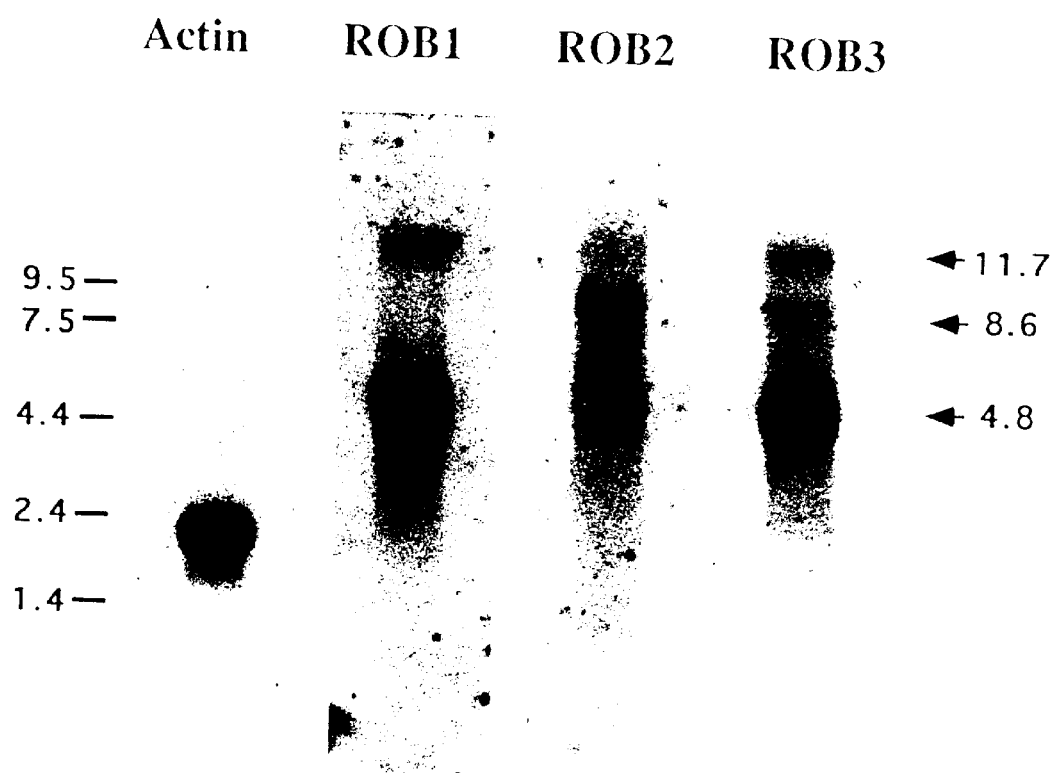
FIG.3 is an autoradiogram of a Northern blot of RNA hybridized to UMR-106, calcium channel riboprobes. A riboprobe corresponding to clones ROB2 was hybridized to poly (A$^+$) RNA (10 $\mu$g/lane) isolated from UMR-106 cells. The actin riboprobe was hybridized to one-tenth as much RNA (1 $\mu$g/lane). Autoradiography was for 67 hours (ROBs) or 6 hours (actin). The actin riboprobe, which was used as a control, hybridized to a single mRNA band of approximately 2.0 kB. An RNA ladder (Gibco/BRL) was used for size markers (in Kilobases).

Northern analysis was used to detect expression of mRNA transcripts corresponding to the UMR-106 calcium channel clones (FIG. 3). (Three sizes of mRNAs of approximately 11.7, 8.6, and 4.8 kB were detected.) The ROB2 clone hybridized predominately to the 8.6 kB MRNA, which is the expected size for a CaCh2 isoform transcript. However a larger 12–15 kB transcript detected in other tissues (22,26, 27), including cardiac muscle, aorta, and brain, was not seen. Very high stringency was used during Northern analysis to maximize the specificity of hybridization. Nevertheless, it is possible that the high degree of sequence identity (approximately 76%) between each of the three CaCh isoforms in the region cloned may be responsible for some cross-hybridization as a result of the relatively high abundance of those transcripts.

EXAMPLE 2

METHODS

Cell culture: UMR-106.01 cells (passages 12–18) were grown in Minimal Essential Medium with Eagles modification, non-essential amino acids and Earle's salts (Sigma, St. Louis, Mo.) supplemented with 10% fetal bovine serum (Gibco, Grand Island, N.Y.). Cells were plated onto flexible, type I collagen-coated, silicone-bottomed 6 well culture plates (Flexcell, Inc., McKeesport, Pa.), fed twice weekly and maintained in a humidified atmosphere of 95% air/5% $CO_2$ at 37° C. When the cells were approx. 75% confluent, they were transfected with either the sense or antisense oligodeoxynucleotides (oligonucleotide) as described below. Culture plates were placed on the Flexercell apparatus which uses vacuum to stretch the silicone bottoms and cyclic stretch was applied for 12–30 hrs at 3 cycles/min. A maximal strain of 12% displacement was applied at the edge of the culture plate falling to 0% displacement at the center.

Transfection of oligonucleotide's. Two antisense oligonucleotides (24-mer and 20-mer)(respectively, SEQ ID NO: 2 and NO: 3) and a sense (24-mer) oligonucleotide were developed from the sequence of a cDNA clone of the $\alpha_1$ subunit of an L-type calcium channel (CaCh2) isolated from UMR-106 by reverse transcriptase-polymerase chain reaction (SEQ ID NO:1). The antisense oligonucleotides were commercially synthesized by Macromolecular Resources (Fort Collins, Colo.). The antisense oligonucleotides were introduced into the UMR cells using streptolysin O (Sigma, St. Louis, Mo.) permeabilization. After the UMR cells had been plated onto the flexible, silicone-bottomed culture plates and grown to 75% confluency, the medium was removed and the cells were washed with a permeabilization buffer consisting of (in mM): 137 NaCl, 5.6 glucose, 2.7 KCl, 2.7 EGTA, 1 Na-ATP, 100 PIPES and 0.1% bovine serum albumin, pH 7.4. The permeabilization buffer containing 0.5 U/ml strptolysin O and 100 μM of the appropriate oligonucleotide was then placed on the cells for 5 min at room temperature. This solution was then removed and the normal medium with 10% fetal bovine serum was added to the cells. For control experiments, UMR cells were permeabilized with the same concentration of streptolysin 0 with no oligonucleotide present.

Patch Clamp Studies. Following application of chronic, intermittent strain, the silicone bottom of the cluster was removed and transferred to a recording chamber (1 ml total volume (Biophysica Technologies, Baltimore, Md.) which was modified to permit rapid exchange of the bathing solution with minimal perturbation to the cells. Cells were bathed in a mammalian Na$^+$ Ringer's solution consisting of (in mM): 136 NaCl; 5.5 KCl; 1 MgCl$_2$; 1 CaCl$_2$; and 20 N-[2-hydroxyethyl]piperazine-N'-[2-ethane sulfonic acid] (HEPES) buffer; titrated to pH 7.3 with NaOH. The strain pattern associated with the Flexcell apparatus is non-uniform (1). The profiles of strain range from 120,000 μE at the edge of the well (12% maximal displacement) to 0 μE at the center. The cells used in this study were subjected to similar magnitudes of strain since patches were always performed in an area 10mm from the edge of the well. Strain applied to this area estimated at 10,000 to 20,000 μE using the strain curve described by Banes, et al. Comparisons were made between chronically stretched control and oligonucleotide-treated cells from the same passage number and at the same level of confluency. To impose membrane strain on the UMR cells during the patch clamp studies, 10 ml 65 mM NaCl (182 mOsm) hypotonic Ringer's solution was perfused into the chamber.

To measure membrane potentials and whole cell conductances, the nystatin performed patch technique was used under current clamp conditions. The pipette solution in these experiments consisted of (in mM): 12 NaCl; 64 KCl; 28 K$_2$SO$_4$; 47 sucrose; 1 MgCl$_2$; 0.5 EGTA; 20 HEPES; titrated to 7.35 with KOH. Nystatin was added at a concentration of 300 μg/ml to permeabilize the patch. Access resistances of <40 MΩ were consistently achieved with this concentration of nystatin. Whole cell conductance measurements were made by pulsing ±50 pA across the membrane.

RESULTS

Figure 4A:
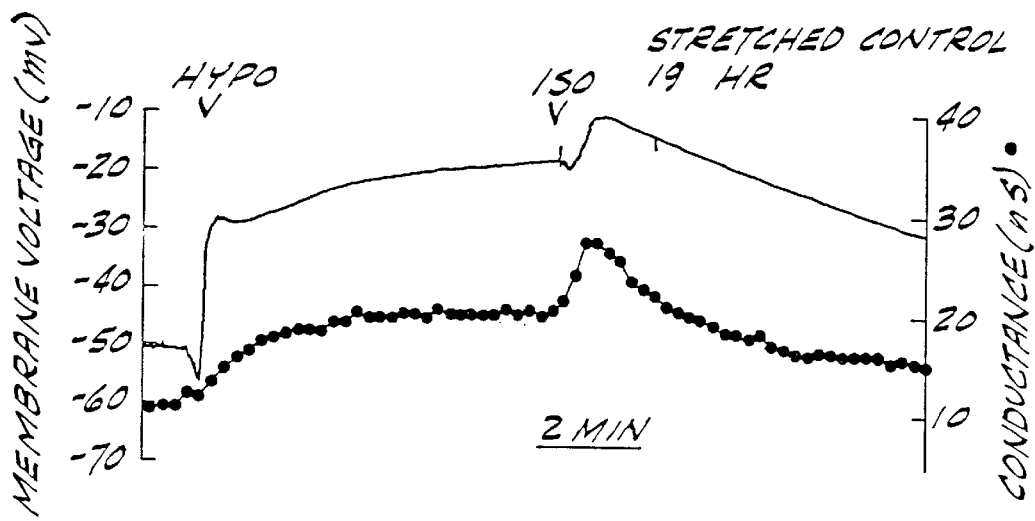
FIGS. 4(a) and 4(b) are graphic representations of the effect of a preferred antisense 24mer oligonucleotide from the $\alpha_1$ subunit of the voltage-gated calcium channel gene (SEQ ID NO.:2) on the response of membrane potential and whole cell conductance to hypotonic stretch.
Figure 4B:
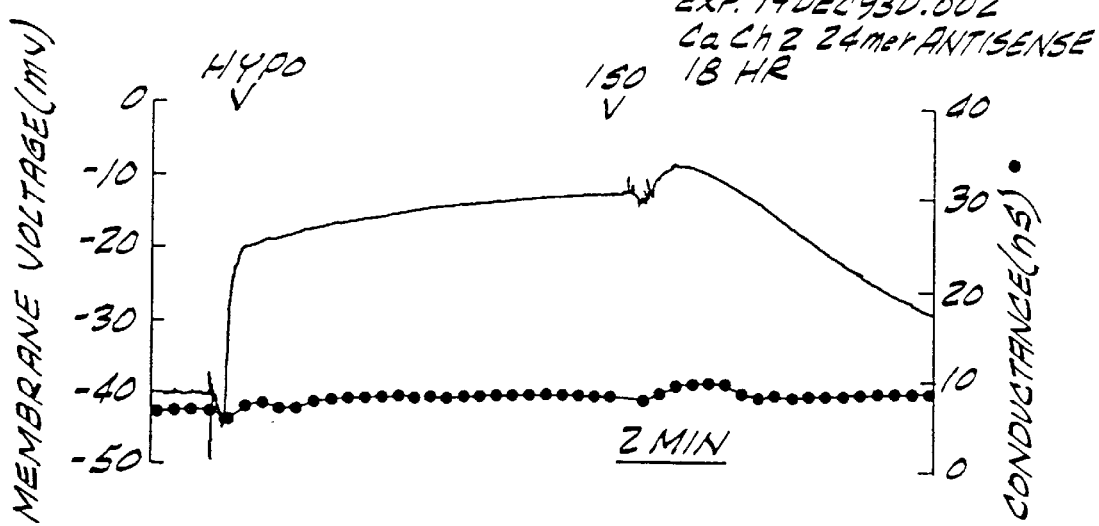
Figure 5A:
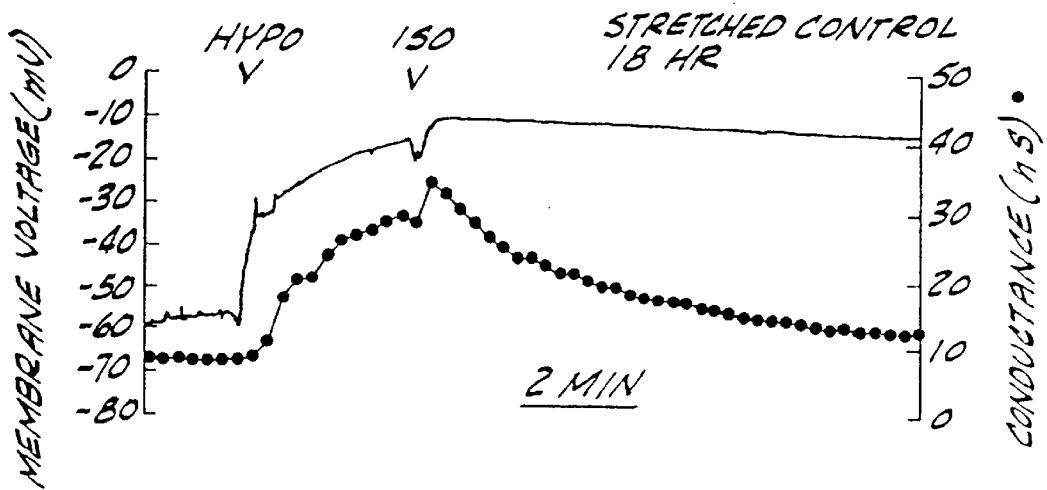
FIGS. 5(A) and 5(B) are graphic representations of the effect of a preferred antisense 20mer oligonucleotide from the $\alpha_1$ subunit of the voltage-gated calcium channel gene (SEQ ID NO.:3) on the response to hypotonic stretch.
Figure 5B:
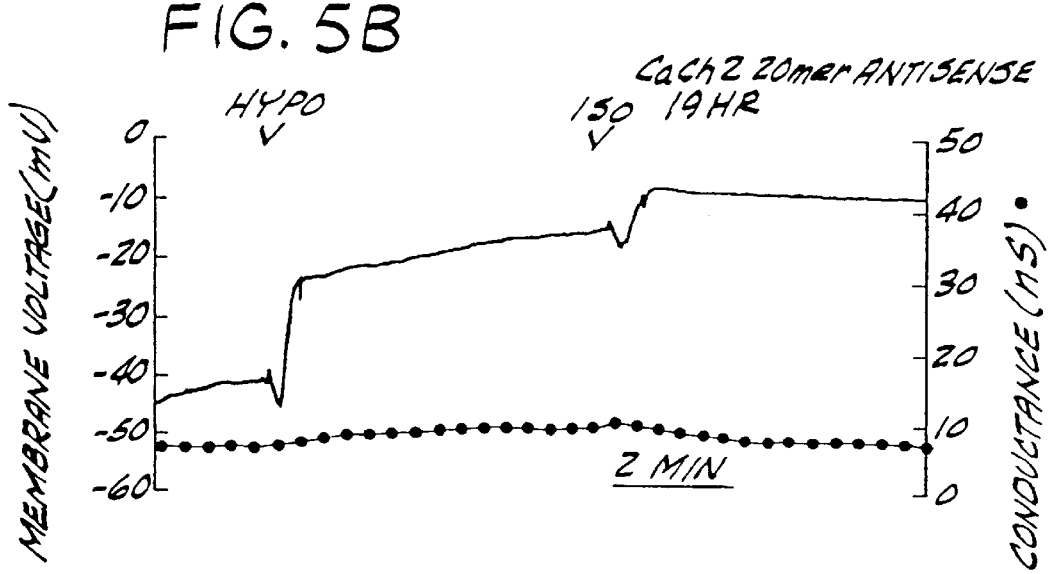

We examined the effects of the antisense and sense oligonucleotides on the strain-induced increase in whole cell conductance in UMR-106.01 cells, which we have shown to be the result of upregulation of the stretch activated cation channel. A previous report had demonstrated that antisense oligonucleotides produce a time dependent inhibition of the chlorothiazide-induced increase in [CaU$^{2+}$]$_i$ in the mouse distal convoluted tudbule cells. This inhibition starts 6 hrs after introduction of the antisense and peaks at 18 hrs. The delay in inhibition was attributed to the turnover of existing proteins prior to the inhibition of new synthesis by the antisense. Cell conductance measurements of the strained UMR cells which had been transfected with the 24-mer antisense found a similar time dependence which began at 12 hr. Measurements at 18 hr found 100% inhibition of the strain-induced increase in whole cell conductance (FIGS. 4(a), 4(b)). Parallel time control cells which had been sham permeabilized exhibited no decrease in whole cell conductance. A similar time course and inhibition was observed for the 20 mer antisense (FIGS. 5(A), 5(B)). Transfection of the sense oligonucleotide produced no significant changes in the whole cell conductance increases associated with hypotonic swelling (FIG. 6). Return of the whole cell conductance response to hypotonicity was observed 26 hr following introduction of the antisense oligonucleotides. This response was significantly higher than the control response, suggesting some feedback mechanism on the gene to increase expression of this protein.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

---

What is claimed is:

1. An antisense oligonucleotide that hybridizes with a region of a voltage-gated calcium channel $\alpha_1$ subunit mRNA and inhibits strain-induced increase in whole cell conductance in osteoblasts, having a sequence selected from the group consisting of SEQ ID NO:2 and SEQ ID NO:3.

2. The antisense oligonucleotide of claim 1, which is DNA.

3. The antisense oligonucleotide of claim 1 in which at least one of the internucleotide linkages is a phosphorothioate phosphodiester.

4. The antisense oligonucleotide of claim 1 further characterized in that it does not hybridize with a CaCh1 or CaCh3 mRNA.

5. A pharmaceutical composition comprising at least one antisense oligonucleotide that hybridizes with a region of a voltage-gated calcium channel $\alpha_1$ subunit mRNA and inhibits strain-induced increase in whole cell conductance in osteoblasts, having a sequence selected from the group consisting of SEQ ID NO:2 and SEQ ID NO:3, and a pharmaceutically acceptable carrier.

6. The pharmaceutical composition of claim 5, wherein the antisense oligonucleotide is DNA.

7. The pharmaceutical composition of claim 5, wherein at least one of the internucleotide linkages is a phosphorothioate phosphodiester.

8. A method of inhibiting expression of a voltage-gated calcium channel $\alpha_1$ subunit gene in a cell, the method comprising the steps of:

(a) obtaining an antisense oligonucleotide that hybridizes with a region of a voltage-gated calcium channel $\alpha_1$ subunit mRNA and inhibits expression of said $\alpha_1$ subunit, having a sequence selected from the group consisting of SEQ ID NO:2 and SEQ ID NO:3, (b) combining said antisense oligonucleotide with a pharmaceutically acceptable carrier to create a pharmaceutically active mixture, and (c) contacting said voltage-gated calcium channel $\alpha_1$ subunit mRNA within said cell in vitro with said pharmaceutically active mixture, thereby inhibiting expression of said voltage-gated calcium channel $\alpha_1$ subunit gene within said cell.

9. The method of claim 8, wherein said cell is an osteoblast or an endothelial cell.

10. A method of inhibiting expression of a voltage-gated calcium channel $\alpha_1$ subunit in a cell, comprising contacting said cell in vitro with an oligonucleotide having the sequence shown in SEQ ID NO:2 or SEQ ID NO:3.

11. The method of claim 10, wherein said cell is an osteoblast or an endothelial cell.

* * * * *